(12) United States Patent
Kline et al.

(10) Patent No.: US 7,384,415 B2
(45) Date of Patent: Jun. 10, 2008

(54) ABSORBENT ARTICLE WITH IMPROVED SURFACE FASTENING SYSTEM

(75) Inventors: Mark J. Kline, Okeana, OH (US); Luke R. Magee, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 208 days.

(21) Appl. No.: 10/774,259

(22) Filed: Feb. 6, 2004

(65) Prior Publication Data
US 2004/0158224 A1     Aug. 12, 2004

Related U.S. Application Data

(63) Continuation of application No. 09/918,265, filed on Jul. 30, 2001, now Pat. No. 6,755,809, and a continuation-in-part of application No. 09/633,422, filed on Aug. 7, 2000, now abandoned, and a continuation-in-part of application No. 09/633,423, filed on Aug. 7, 2000, now Pat. No. 6,911,023.

(51) Int. Cl.
A61F 13/56     (2006.01)
A61F 13/62     (2006.01)
(52) U.S. Cl. .................. 604/390; 604/385.31; 604/391
(58) Field of Classification Search ................ 604/386, 604/390, 385.31, 387
See application file for complete search history.

(56) References Cited

U.S. PATENT DOCUMENTS

| | | | | |
|---|---|---|---|---|
| 1,385,311 A * | 7/1921 | DuPont | ......................... | 16/10 |
| 2,477,914 A * | 8/1949 | Webb | ......................... | 604/386 |
| 3,241,881 A * | 3/1966 | Rice et al. | .................. | 297/468 |
| 3,256,882 A | 6/1966 | Huber | | |
| 3,322,455 A * | 5/1967 | Gressbach | .................. | 294/104 |
| 3,370,560 A * | 2/1968 | Lucht | ...................... | 114/39.23 |
| 3,531,835 A * | 10/1970 | Paikin | ......................... | 24/516 |
| 3,860,003 A | 1/1975 | Buell | | |
| 4,085,746 A * | 4/1978 | Castiglia | ...................... | 602/65 |
| 4,090,516 A * | 5/1978 | Schaar | ....................... | 604/390 |
| 4,158,906 A * | 6/1979 | Watson | ........................ | 24/306 |
| 4,324,429 A * | 4/1982 | Wilson et al. | ........... | 296/100.1 |

(Continued)

FOREIGN PATENT DOCUMENTS

CA     2 278 867     3/2000

(Continued)

Primary Examiner—Tatyana Zalukaeva
Assistant Examiner—Paula L. Craig
(74) Attorney, Agent, or Firm—Thibault Fayette; Jay Krebs; Matthew P. Fitzpatrick

(57) ABSTRACT

An article having a surface fastening system and a primary direction of load bearing. The surface fastening system includes at least one first fastening element and at least on second fastening element. The first fastening element further includes an attached portion, partially joined to the article, at least one liftable portion extending from the attached portion, and at least one hinge line disposed at an angle less than 90 degrees relative to the primary direction of load bearing, the hinge line is positioned between the attached portion and the liftable portion. At least one second fastening element is affixed at a second position to the article and configured to be engageable with the liftable portion of the first fastening element. Articles such as disposable diapers, bibs, clothing, etc. are disclosed.

15 Claims, 13 Drawing Sheets

U.S. PATENT DOCUMENTS

| | | | |
|---|---|---|---|
| 4,555,244 A * | 11/1985 | Buell | 604/392 |
| 4,573,986 A | 3/1986 | Minetola et al. | |
| 4,576,154 A * | 3/1986 | Hyman et al. | 602/19 |
| 4,578,072 A * | 3/1986 | Lancaster | 604/385.24 |
| 4,699,621 A * | 10/1987 | Stevens et al. | 604/385.29 |
| 4,733,658 A * | 3/1988 | Ruthven, Jr. | 602/4 |
| 4,785,996 A | 11/1988 | Ziecker et al. | |
| 4,842,666 A | 6/1989 | Werenicz | |
| 4,886,231 A * | 12/1989 | Doerksen | 248/455 |
| 4,892,536 A | 1/1990 | Desmarais et al. | |
| 4,893,381 A * | 1/1990 | Frankel | 24/16 R |
| 4,895,569 A * | 1/1990 | Wilson et al. | 604/386 |
| 4,990,147 A | 2/1991 | Freeland | |
| 5,037,416 A | 8/1991 | Allen et al. | |
| 5,049,145 A * | 9/1991 | Flug | 604/391 |
| 5,053,028 A * | 10/1991 | Zoia et al. | 604/385.21 |
| 5,076,288 A * | 12/1991 | Millard et al. | 128/869 |
| 5,100,399 A * | 3/1992 | Janson et al. | 604/386 |
| 5,151,092 A | 9/1992 | Buell et al. | |
| 5,171,236 A | 12/1992 | Dreier et al. | |
| 5,221,274 A | 6/1993 | Buell et al. | |
| 5,260,345 A | 11/1993 | Desmarais et al. | |
| 5,267,992 A | 12/1993 | Van Tilburg | |
| 5,269,775 A | 12/1993 | Freeland et al. | |
| 5,286,112 A | 2/1994 | Bible | |
| 5,304,162 A * | 4/1994 | Kuen | 604/391 |
| 5,318,555 A * | 6/1994 | Siebers et al. | 604/390 |
| 5,325,415 A | 6/1994 | Coffman | |
| 5,342,338 A | 8/1994 | Roe | |
| 5,375,534 A * | 12/1994 | Adams | 105/372 |
| 5,387,207 A | 2/1995 | Dyer et al. | |
| 5,389,094 A | 2/1995 | Lavash et al. | |
| 5,397,316 A | 3/1995 | Lavon et al. | |
| 5,514,121 A | 5/1996 | Roe et al. | |
| 5,518,801 A | 5/1996 | Chappell et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,521 A * | 1/1997 | Arakawa et al. | 428/352 |
| 5,603,794 A * | 2/1997 | Thomas | 156/256 |
| 5,625,222 A | 4/1997 | Yoneda et al. | |
| 5,741,318 A | 4/1998 | Ouellette et al. | |
| 5,860,945 A | 1/1999 | Cramer et al. | |
| 5,865,823 A | 2/1999 | Curro | |
| 5,873,870 A | 2/1999 | Seitz et al. | |
| 5,897,545 A * | 4/1999 | Kline et al. | 604/386 |
| 5,928,212 A * | 7/1999 | Kline et al. | 604/391 |
| 5,938,648 A | 8/1999 | Lavon et al. | |
| 5,968,031 A * | 10/1999 | Schmitz | 604/391 |
| 5,977,430 A | 11/1999 | Roe et al. | |
| 5,987,545 A | 11/1999 | Oh | |
| 6,004,306 A * | 12/1999 | Robles et al. | 604/385.21 |
| 6,010,491 A | 1/2000 | Roe et al. | |
| 6,053,308 A * | 4/2000 | Vogrig et al. | 198/844.2 |
| 6,054,091 A | 4/2000 | Miller et al. | |
| 6,102,901 A * | 8/2000 | Lord et al. | 604/386 |
| 6,413,249 B1 * | 7/2002 | Turi et al. | 604/387 |
| 6,454,751 B1 * | 9/2002 | Olson | 604/389 |
| 6,463,633 B1 * | 10/2002 | Sangani et al. | 24/304 |
| 6,554,816 B1 * | 4/2003 | Olson | 604/386 |
| 6,579,275 B1 * | 6/2003 | Pozniak et al. | 604/390 |
| 6,755,809 B2 * | 6/2004 | Kline et al. | 604/390 |
| 6,764,480 B2 * | 7/2004 | Tani et al. | 604/391 |
| 6,911,023 B1 * | 6/2005 | Hamilton et al. | 604/387 |
| 2002/0173765 A1 * | 11/2002 | Pargass et al. | 604/386 |
| 2004/0013852 A1 | 1/2004 | Curro et al. | |
| 2004/0147899 A1 | 7/2004 | Kline et al. | |
| 2007/0142815 A1 * | 6/2007 | Macura et al. | 604/389 |
| 2007/0143972 A1 * | 6/2007 | Kline et al. | 24/442 |

FOREIGN PATENT DOCUMENTS

| | | |
|---|---|---|
| EP | 0 786 243 A2 | 7/1997 |
| WO | WO 1995/016746 A1 | 6/1995 |

* cited by examiner

ABSORBENT ARTICLE WITH IMPROVED SURFACE FASTENING SYSTEM

This application is a continuation of prior application Ser. No. 09/918,265 filed Jul. 30, 2001 now U.S. Pat. No. 6,755,809. This application also is a continuation-in-part of prior application Ser. No. 09/633,422 filed Aug. 7, 2000 now abandoned and prior application Ser. No. 09/633,423 filed Aug. 7, 2000 now U.S. Pat. No. 6,911,023.

FIELD OF THE INVENTION

The present invention also relates to articles such as diapers, training pants, bibs, sanitary napkins and the like with an improved surface fastening system.

BACKGROUND OF THE INVENTION

Articles, absorbent articles and disposable absorbent articles such as diapers, training pants, bibs, sanitary napkins and the like are well known in the art. Such absorbent articles are typically used to absorb and contain bodily exudates such as feces, urine and/or menses, foods, or other substances. Until fairly recently, many of the absorbent articles identified above were made from reusable materials such as woven cloth materials including cotton and other absorbent fabrics. Many consumers have found that using disposable absorbent articles is more convenient than using reusable articles for various reasons. Accordingly, many different types of disposable absorbent articles, including disposable diapers such as those described in U.S. Pat. No. 5,151,092 entitled "Absorbent Article with Dynamic Elastic Waist Feature having Predisposed Flexural Hinge" issued to Buell et al. on Sep. 22, 1992 have achieved wide acceptance and commercial success.

Over the years, there have been many advancements related to disposable absorbent articles, including improvements in fastening systems, absorbency, and aesthetics. However, there is still a need for improvement relating to fit, comfort, aesthetics, and overall performance of such articles. For example, disposable diapers often do not look or feel like garments. Further, disposable diapers are often difficult for the user, whether it be the caregiver or child, to properly fasten about the wearer. This can lead to poor fit, which can result in leaks and/or reduced comfort for the wearer. Further, in diapers for active wearers and in refastenable pull-on diapers, such as described in U.S. Pat. No. 5,987,545 issued to Kline et al., multi-directional resistance to disengagement is important to ensure that the fasteners remain engaged while pulling up and/or wearing the diaper.

Accordingly, it would be desirable to provide an absorbent article with an improved fastening system. It would also be desirable to provide an absorbent article with lower cost fastening system. It would also be desirable to provide an absorbent article with improved fit, aesthetics, and overall performance. Further, it would be desirable to provide an absorbent article with an improved fastening system that provides easier and more reliable fastening performance including improved resistance to disengagement during article use, thus requiring less fastening material than the prior art, for the same level of fastening security.

SUMMARY OF THE INVENTION

The present invention provides an article to be fastened together, and in alternate embodiments, to be worn about a wearer. The invention includes a surface fastening system having a primary direction of load bearing. The surface fastening system has at least one first fastening element, and at least one second fastening element. The first fastening element includes an attached portion joined to the article, at least one liftable portion extending from the attached portion, and at least one hinge line positioned between the attached portion and the liftable portion. The hinge line is disposed at an angle less than 90 degrees relative to the primary direction of load bearing. The second fastening element is affixed at a second position to the article and is configured such that at least a portion of the second fastening element is releasably engageable with at least a portion of the liftable portion of the first fastening element.

In alternate embodiments, the second fastening element may also be partially joined to the article and include a liftable portion. The surface fastening system may have a peel load capacity during use which is greater than or equal to about 1000 grams. A functional model of peel resistance is used to describe and claim preferred embodiments of the invention. The first fastening element liftable portion improves the overall load carrying capacity of the surface fastening system during article use. The surface fastening system preferably delivers improved multidirectional resistance to surface fastening system disengagement during use. Many variations of the invention are possible, of which several are specifically disclosed herein.

BRIEF DESCRIPTION OF THE DRAWINGS

While the specification concludes with claims particularly pointing out and distinctly claiming the subject matter which is regarded as forming the present invention, it is believed that the invention will be better understood from the following description when taken in conjunction with the accompanying drawings, in which:

The drawings are for the purpose of illustration and are not necessarily drawn to scale. Like reference numbers have been used to indicate like components in the drawings.

DETAILED DESCRIPTION OF THE INVENTION

As used herein, the term "article" refers to any article including a bib, diaper, sanitary napkin, medical bandage, utility belt, sling, absorbent article, or other device which carries load through a surface fastening system when the fastening elements are engaged. The bib for example could be a child's bib fastened in the back. The sling may be a sling for a broken arm that holds the arm in a place.

As used herein, the term "absorbent article" refers to devices that absorb and contain body exudates and, more specifically, refers to devices that are placed against or in proximity to the body of a wearer to absorb and contain the various exudates discharged from the body. The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner). A "unitary" absorbent article refers to absorbent articles which are formed of separate parts united together to form a coordinated entity so that they do not require separate manipulative parts like a separate holder and/or liner. As used herein, the term "diaper" refers to an absorbent article generally worn by infants and incontinent persons about the lower torso. The present invention is also applicable to other absorbent articles such as incontinence briefs, pull-ups, prefastened diapers, refastenable diapers, incontinence undergarments, absorbent inserts, diaper holders and liners, feminine hygiene garments, wipes, mops, bandages and the like.

Figure 1:
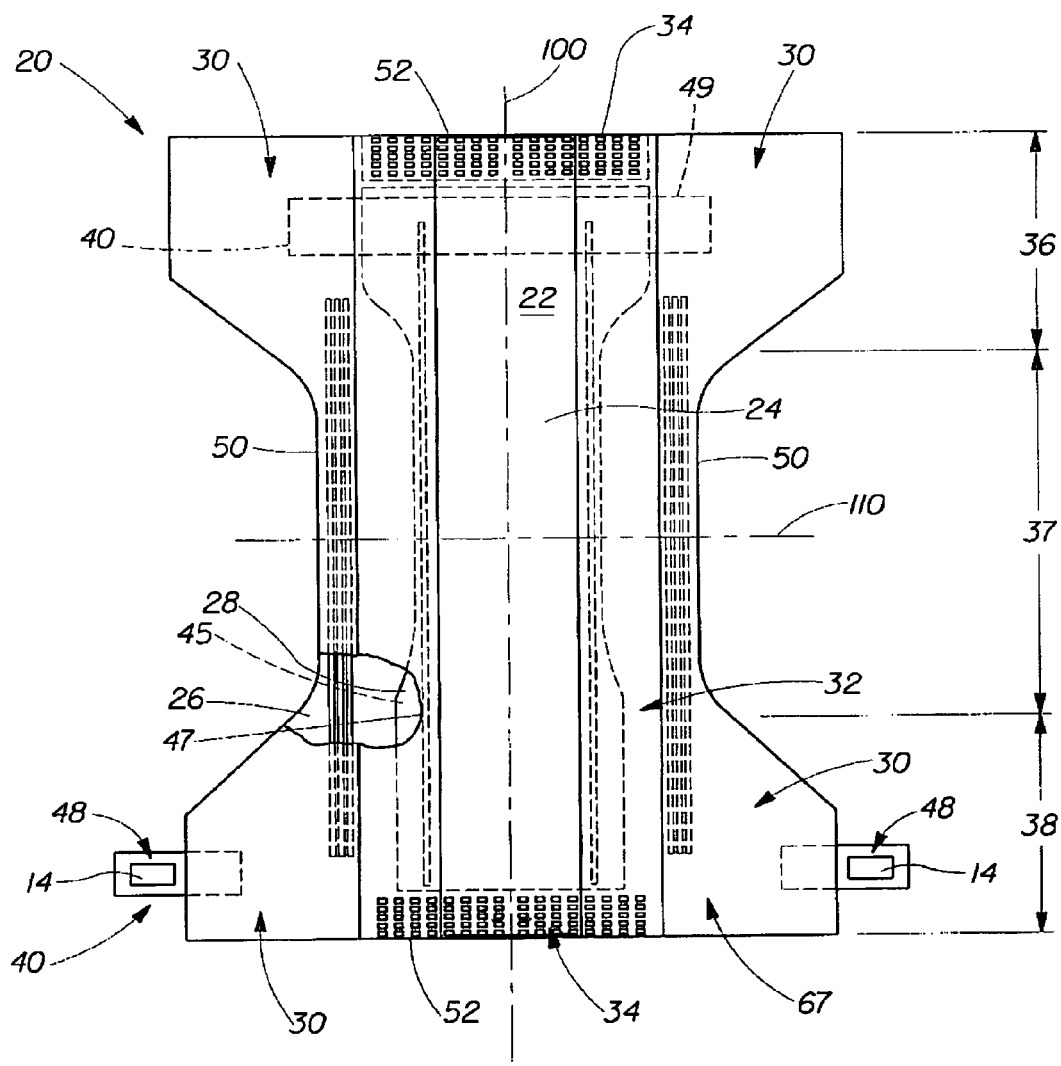
FIG. 1 is a plan view of one embodiment of the present invention as a diaper in a flat configuration with portions of the structure cut-away to show the construction the article.

FIG. 1 is a plan view of one embodiment of the article as a diaper 20 in a flat configuration with portions of the structure being cut-away to show the construction of the diaper 20. The portion of the diaper 20, which faces the wearer, is oriented towards the viewer. As shown in FIG. 1, the diaper 20 preferably comprises a liquid previous topsheet 24; a liquid impervious backsheet 26; an absorbent core 28 which is preferably positioned between at least a portion of the topsheet 24 and the backsheet 26; opposite side panels 30; elasticized leg cuffs 32; a waist feature 34; and a surface fastening system 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering including the topsheet 24 and/or the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet 24, a backsheet 26, and an absorbent core 28. In such cases, the holder and/or the liner may include a holding element, which is used to hold the liner in place throughout the time of use.) For unitary absorbent articles, the chassis 22 comprises the main structure of the diaper 20 with other features added to form the composite diaper structure. While the topsheet 24, the backsheet 26, and the absorbent core 26 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The backsheet 26 is generally that portion of the diaper 20 positioned adjacent garment facing surface 45 of the absorbent core 28 that prevents exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials, which permit vapors to escape from the diaper 20 while still preventing exudates from passing through the backsheet 26. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097. Some breathable composite materials are described in greater detail in PCT application Ser. No. WO 95/16746 published on Jun. 22, 1995 in the name of E. I. DuPont; U.S. Pat. No. 5,938,648 issued on Aug. 17, 1999 to LaVon et al.; U.S. Pat. No. 5,865,823 issued on Feb. 2, 1999 in the name of Curro; and U.S. Pat. No. 5,571,096 issued to Dobrin et al. on Nov. 5, 1996. Each of these references is hereby incorporated by reference herein.

The backsheet 26 or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. (As used herein, the term "joined" encompasses configurations whereby an element is directly secured to another element by affixing the element directly to the other element, and configurations whereby an element is indirectly secured to another element by affixing the element to intermediate member(s) that in turn are affixed to the other element.) For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Satisfactory adhesives include those manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to one or more other elements of the diaper 20.

The topsheet 24 is preferably compliant, soft feeling, and non-irritating to the wearer's skin. Further, at least a portion of the topsheet 24 is liquid pervious, permitting liquid to readily penetrate through its thickness. A suitable topsheet 24 may be manufactured from a wide range of materials, such as porous foams, reticulated foams, apertured plastic films, or woven or nonwoven materials of natural fibers (e.g., wood or cotton fibers), synthetic fibers (e.g., polyester or polypropylene fibers), or a combination of natural and synthetic fibers. If the topsheet 24 includes fibers, the fibers may be spunbond, carded, wet-laid, meltblown, hydroentangled, or otherwise processed as is known in the art. One suitable topsheet 24 comprising a web of staple-length polypropylene fibers is manufactured by Veratec, Inc., a Division of International Paper Company, of Walpole, Mass. under the designation P-8.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein. Preferably, at least a portion of the topsheet 24 is made of a hydrophobic material or is treated to be hydrophobic in order to isolate the wearer's skin from liquids contained in the absorbent core 28.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent assemblies are described in U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear. The diaper 20 may also comprise at least one waist feature 34 that helps to provide improved fit and containment. The waist feature 34 may be elastic and/or extensible, or neither elastic or extensible.

Embodiments of the present invention may also include pockets for receiving and containing waste, spacers which provide voids for waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer," and U.S. Pat. No. 5,171,236 issued to Dreier et al. on Dec. 15, 1992 entitled "Disposable Absorbent Article Having Core Spacers."

The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092, which are incorporated by reference herein. In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

The article may also include a surface fastening system 40. On a diaper 20, the surface fastening system 40 preferably maintains the first waist region 36 and the second waist region 38 in a configuration so as to provide lateral tensions about the circumference of the diaper 20 to hold the diaper 20 on the wearer. This lateral tension may be in a primary direction of load bearing when the fastening system 40 engages the first waist region 36 and the second waist region 38. In a diaper 20, the primary direction of load bearing is generally in the direction of the fastening load carried by the surface fastening system 40 when the fastening system 40 is in use. This is typically a shear load between the first fastening element 49 located in the first waist region 36 and the second fastening element 48 located in the second waist region 38 when the surface fastening system is engaged. The peel load direction on a diaper 20 is generally a direction between the primary direction of load bearing and a direction normal to the primary direction of load bearing.

Figure 2:
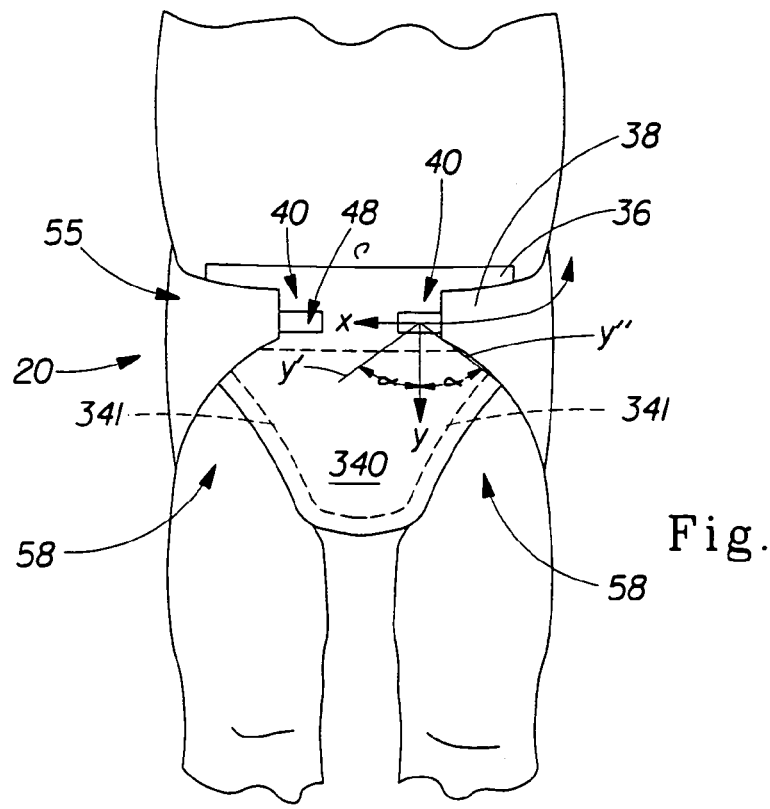
FIG. 2 is a perspective view of one embodiment of the present invention fastened about a wearer.

The present invention allows the fastening elements to reorient themselves as various loads are applied during use. In a most basic description, the surface fastening system 40 allows a first fastening element 49 and a second fastening element 48 to at least partially reorient under load such that rather than being in a peel relationship with a load (peel mode), they at least partially lift into at least a partial shear relationship with the load. Thus, the surface fastening system 40 is capable of staying fastened under a greater peel load than otherwise possible. In at least one embodiment when the diaper 20 is fastened about the wearer, the second fastening elements 48 on the side panels 30 of the second waist region 38 engage the first fastening element(s) 49 disposed in the first waist region 36 to fasten the second waist region 38 to the first waist region 36. When the first fastening element 49 and second fastening element 48 shown in FIG. 1 are attached, a pant-like article is formed having a waist hoop 55 and a pair of leg openings 58 as shown in FIG. 2.

For a diaper 20, the surface fastening system 40 preferably comprises two or more second fastening elements 48 as shown in FIG. 1. In FIG. 1, second fastening element 48 is disposed on one of the two side panels 30 in the second waist region 38. The second fastening element 48 may be disposed in the second waist region 38 on the inner surface 67, on the backsheet 26, or otherwise attached to the side panel 30 in the second waist region 38 in any fashion known in the art. The second fastening element 48 may either be discrete separate elements affixed to the diaper 20 or a unitary piece of material that is neither divided nor discontinuous with an element of the diaper 20.

The present invention, in an embodiment such as a diaper 20, may provide an improved balance between skin marking and leg freedom when the article is properly fitted to the wearer. The present invention may further require less retaining element 14 (hook & loop material) for a given level of load caring during use, than a comparable prior art fastening system. When the diaper 20 is applied to a wearer, the first fastening element 49 and the second fastening element 48 of the fastening system 40 may be connected over the front of the wearer's leg with a liftable portion 72 such that the leg may move freely. The fastening system 40 may fasten the article 20 about the wearer with less skin marking or leg restraint than the prior art. While the present invention is particularly useful for the attachment of an absorbent article about a wearer, it also would have application for any article attachment where the applied load direction with respect to the fastener may be manipulated by the hinged approach of the present invention to improve the fastener's ability to remain fastened during use.

In one embodiment the surface fastening system 40 comprises at least one first fastening element 49 and at least one second fastening element 48, the components and location of which are generally interchangeable with one another but may be unique with respect to their respective underlying attachment to the article. As shown in FIG. 1 the first fastening element 49 may be located on the first waist region 36 and the second fastening element 48 may be located on the second waist region 38. The first fastening element 49 and the second fastening element 48 may have a retaining element 14 or other means for releasably engaging the first fastening element 49 and the second fastening element 48. Engaging includes holding the first fastening element 49 and second fastening element 48 together when the two are fastened. Adhesives, and hook and loop are two common types of retaining elements. Generally, any known retaining element 14 suitable for a surface fastening system 40 is acceptable. More details concerning the retaining element are discussed below. Interlocking fasteners such as buttons, zippers, buckles and the like, however, are not surface fastening systems 40, or retaining elements 14 suitable for a surface fastening system 40.

Figure 8:
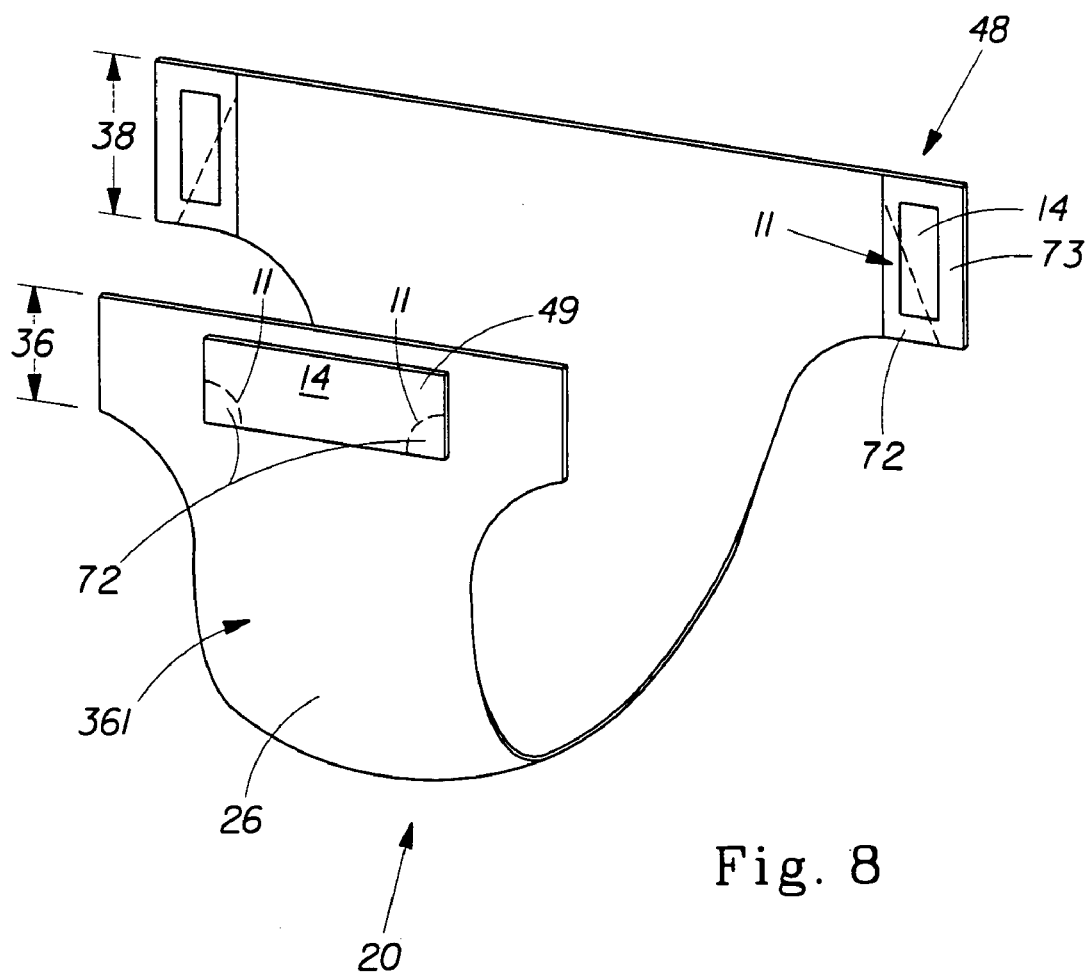
FIG. 8 is a perspective view of one embodiment of the article as a diaper.

In a diaper configuration as shown in FIG. 8, the first fastening element 49 may comprise at least one attached portion 73 which is attached to the article 20, and at least one liftable portion 72. The liftable portion 72 is liftable from the article 20 and extends from the attached portion with a hinge line 11, which extends between the liftable portion 72 and attached portion 73. The second fastening element 48 is generally engageable with the first fastening element 49. The first fastening element 49 and second fastening element 48 engagement may include all, or any portion of either fastening element. The first fastening element 49 may be disposed on the garment facing surface 361 in the first waist region 36. The garment facing surface 361 is generally the article surface which faces the clothing worn by the wearer such as a backsheet 26 or something attached to a backsheet 26 such as a first fastening element 49 or second fastening element 48. Preferably, first fastening element 49 comprises at least one hinge line 11 and at least one liftable portion 72. More preferably, the first fastening element 49 may comprise two hinge lines 11 which are not perpendicular to the primary direction of load bearing, and two liftable portions 72.

First fastening element 49 and second fastening element 48 may comprise a retaining element 14. As generally discussed above, the retaining element 14 may be used to releasably engage the first fastening element 49 and second fastening element 48. The retaining element 14 can include hook and loop, adhesive, cohesive, hermaphroditic, friction, static, and magnetic fasteners, macro-fasteners, and the like. Structural designs such as the fasteners described in U.S. patent application Ser. No. 09/633,422 filed Aug. 7, 2000, by The Procter & Gamble Co. are also contemplated.

The retaining element 14 may be located on the first fastening element 49 and/or the second fastening element 48. The retaining element may be located on the attached portion 73 and/or the liftable portion 72 of either the first or the second fastening element. Preferably, for the first and second fastening elements, at least one retaining element 14 is located at least partially on the liftable portion 72. In one embodiment at least about 5% of the first or second fastening element retaining element 14 is located on the corresponding liftable portion 72 of either the first or second fastening element. Alternatively, at least about 10% of the first or second fastening element retaining element 14 is located on the corresponding liftable portion 72 of either the first or second fastening element. Alternatively, at least about 45% of the first or second fastening element retaining element 14 is located on the corresponding liftable portion 72 of either the first or second fastening element.

Figure 9:
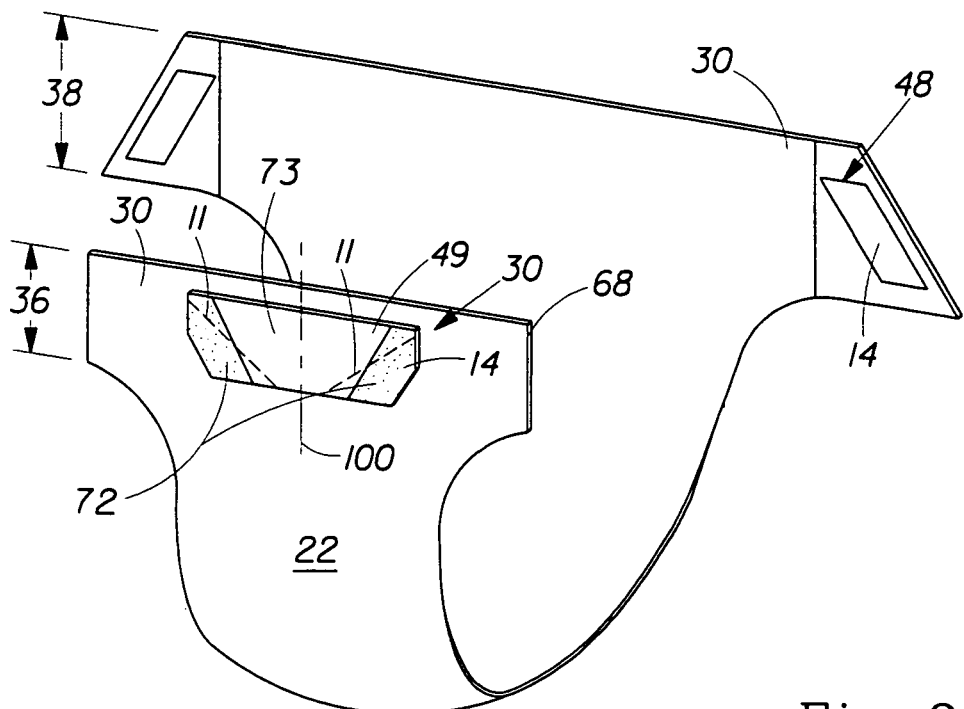
FIG. 9 is a perspective view of one embodiment of the article as a diaper.

The retaining elements 14 on the first fastening element 49 and/or the second fastening element 48 may be disposed at an angle relative to the longitudinal centerline 100 and placed on the liftable portion 72 and/or the attached portion 73. FIG. 9 depicts a diaper embodiment wherein the second fastening element 48 has a retaining element 14 across the entire second fastening element 48. The first fastening element 49 has a retaining element 14 at each end. The retaining element 14 is disposed partially upon the first fastening element 49 liftable portion 72 and partially on the first fastening element 49 attached portion 73.

The retaining element 14 may be one, or more than one piece of material. The retaining element may also be integral to either fastening element. The size, shape, and location of the retaining element 14 may vary. The retaining element 14 may be square, rectangular, trapezoid, circular or any other shape or shapes. Four sample retaining element 14 configurations are shown in FIGS. 5A-5D. FIG. 8 shows the retaining element 14 on the first fastening element 49 overlapping all of the attached portion 73 and liftable portion 72. The second fastening element 48 may also comprise an attached portion 73 that is attached to the article 20, and a liftable portion 72 that is liftable from the article 20 and extends from the attached portion 73 along the hinge line 11. FIG. 8 shows the retaining element 14 on the second fastening element 48 overlapping part of the second fastening element attached portion 73 and part of the second fastening element liftable portion 72.

The first fastening element 49 is attached to the article 20 by attached portion 73. For example, in one embodiment the attached portion 73 would be uniformly attached to the backsheet 26. Alternatively, as shown in FIG. 6C, the attached portion 73 may be attached to the article at one or more discrete locations that together create an area which functions as an attached portion 73 even though some of the first fastening element 49 between the attached portion is not directly attached to the article 20. For example, in FIG. 6C there are multiple attached portions 73, a hinge line 11, a second hinge line 111, a liftable portion 72, and a second liftable portion 172. The liftable portions 72 and 172 are shown in FIG. 6C. The hinge line 11 and second hinge line 111 in FIG. 6C are shown defined by the laterally outboard longitudinal edge of the attached circular portions 73. Attachment of the attached portion 73 to the article 20 may be by any means known in the art including thermal bonding, adhesives, ultrasonic bonding, stitching, or combinations thereof.

Figure 11A:
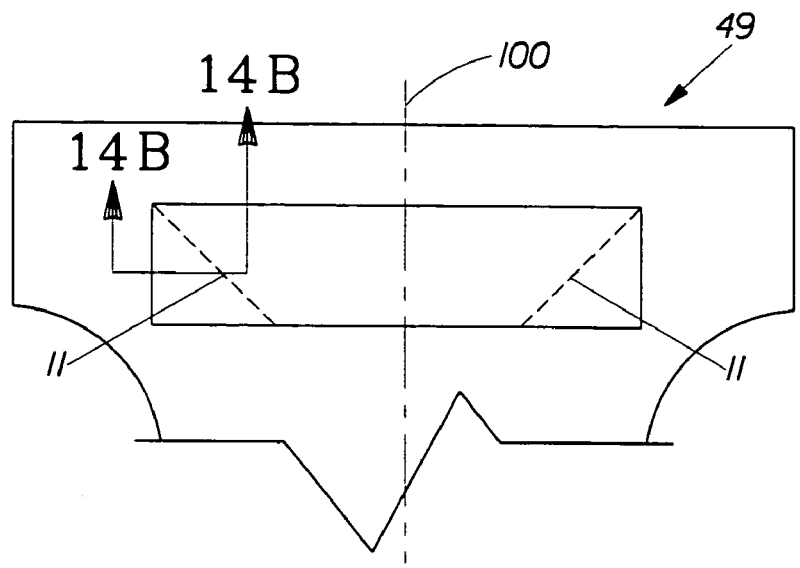
FIG. 11A is a plan view of one embodiment of the first fastening element on a diaper first waist region.
Figure 11B:
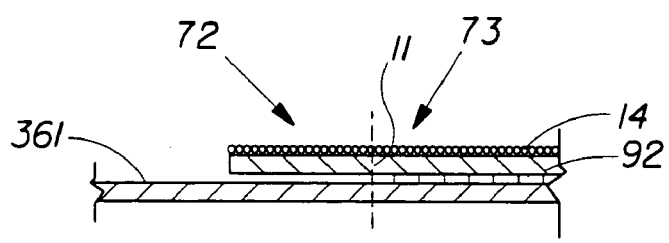
FIGS. 11B-D are a cross-sectional view of the hinge assembly. Note: For clarity the first fastening element is lifted away from the garment facing surface to show the hinge line.
Figure 11C:
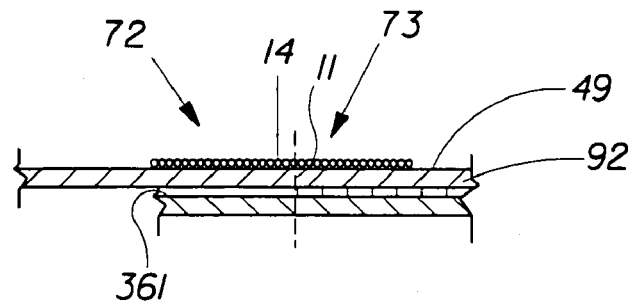
Figure 11D:
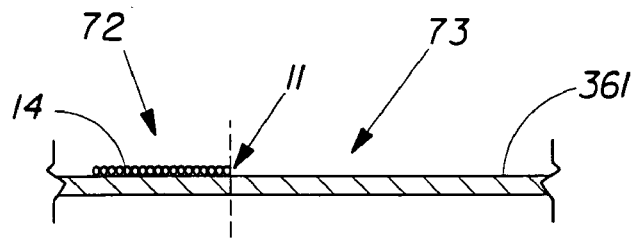

The first fastening element 49 (the landing zone) and/or second fastening element 48 may include a variety of construction combinations, some embodiments of which are shown in FIGS. 11B-11D. The first fastening element 49 and/or second fastening element 48 are generally attached to the article with at least one attached portion 73. The first fastening element 49 and/or second fastening element 48 may include one or more retaining elements 14 attached to the first fastening element 49 by any means known in the art. For clarity in FIGS. 11B-11D, the liftable portion 72 of first fastening element 49 is shown lifted away from the garment facing surface 361 to show the hinge line 11.

Preferably, the first fastening element 49 attached portion 73 is attached to the article 20 on the garment facing surface 361 in the first waist region 36 and the liftable portion 72 lifts from the garment facing surface 361. FIG. 11B shows a cross sectional view of the first fastening element 49 shown in FIG. 11A. FIG. 11B shows a retaining element 14 and a backing 92 disposed between the retaining element 14 and the garment facing surface 361. The backing 92 is connected to the retaining element 14 and the garment facing surface 361 at the attached portion 73. FIG. 11C shows a cross sectional view of the first fastening element 49 shown in FIG. 11A wherein the liftable portion 72 has a backing 92 that extends beyond the retaining element 14. This extension of backing 92 may be used as a grasping point for attaching the first and second fastening elements. FIG. 11D shows a cross sectional view of the first fastening element 49 shown in FIG. 11A wherein the liftable portion 72 is the retaining element 14 without a backing 92.

Embodiments have also been contemplated in which at least a portion of the second fastening element 48, the first fastening element 49, and/or components thereof such as backing 92 or retaining elements 14 include an extensible or elastomeric carrier web. At least a portion of the carrier web may be unjoined from the underlying structure of the article. Any extensible and/or elastomeric/elastic materials, including those previously referenced herein, may be used as the carrier web. One example of a carrier web is a vacuum formed elastomeric material such as described in U.S. patent application Ser. No. 08/816,106 filed on Mar. 14, 1997, which is incorporated herein by reference. An elastomeric or extensible first or second fastening element may contribute to the transfer of peel load to shear load in the fastening system 40.

The hinge line 11 generally separates (lies between) the attached portion 73 and the liftable portion 72. The hinge line 11 may extend in any direction with respect to the longitudinal centerline 100 and the lateral centerline 110 as shown in FIGS. 7, 9 and 14A-14C. Preferably, the hinge line is non-orthogonal to the longitudinal centerline 100 such that it intersects both the longitudinal centerline 100 and the lateral centerline 110. In addition, the hinge line 11 may diverge from the longitudinal centerline 100 as it moves away from the lateral centerline 110 of the absorbent article. More preferably, the hinge line 11 may be intersected by the primary direction of load bearing at an angle less than 90 degrees. One of ordinary skill in the art should understand that if one intersecting angle is less than 90 degrees, the adjacent angle is greater than 90 degrees. Stated more directly, the hinge line 11 is preferably not perpendicular to the primary direction of load bearing.

The hinge line 11 may run generally in a straight line or it may run in any contour. FIGS. 6A-6B, 8, and 14A-14C, show the hinge line 11 with various contours. Part of the hinge line 11 may be parallel to either the longitudinal centerline 100 or the primary direction of load bearing at transition points in some embodiments. For example, where a hinge line 11 is curved, a tangent to the curve may be parallel to the longitudinal centerline 100. In an embodiment such as a diaper 20, a contoured hinge line 11 may preferably follow a path from a point closer to the intersection of the longitudinal centerline 100 and the lateral centerline 110, to a point further away from this intersection in order to provide ease of leg movement under the fastening system 40.

Hinge lines 11 that intersect the longitudinal centerline 100 and the lateral centerline 110 are advantageous. The low motion zone 340 is generally within the low motion zone perimeter 341 defined by the leg creases and belly crease, forming a generally triangularly shaped area in the wearer's pubic area as shown in FIG. 2. Fitting the hinge line 11 in the low motion zone 340 and/or along the perimeter 341 of the low motion zone 340 between the leg opening 58 and the waist hoop 55 optimizes fit and reduces skin marking caused by the diaper 20.

The second fastening element 48 may be fastened to the corresponding first fastening element 49 (landing zone) at an angle between the longitudinal centerline 100 and the lateral centerline 110 and generally along the perimeter 341 of the low motion zone 340 such that leg marking is further reduced and leg freedom of movement is further increased. When the hinge line(s) 11 are angled, as shown in FIGS. 7, 8, and 14A-14D, more material is available for fastener attachment to resist loads in the primary direction of load bearing while still allowing freer movement by the wearer in other directions, e.g. the movement of the wearers legs while wearing a diaper. This may reduce the amount or cost of the fastening system 40 retaining element 14 required to maintain the article in a fastened configuration during use. In addition, placing the liftable portion 72 across the wearer at locations such as the upper thigh may reduce skin marking in that area despite the motions of the wearer. Further, keeping the first fastening element 49 partially attached laterally outboard (resulting from an angled hinge line 11) helps to maintain proper fit during use. The fastening system 40 can for example, straddle the perimeter 341 of the low motion zone 340 between the leg openings 58 and the waist hoop 55 and remain fastened while still allowing freer leg motion and a reduced risk of skin marking during use. In another embodiment, an outward angle of the hinge line 11 provides a fastening point closer to the distal edge 68 of the first waist region 36 as shown in FIG. 9. The angled hinge line 11 may allow less restrained leg movement while still minimizing diaper roping. Roping results when the first waist region 36 and second waist region 38 roll and separate after surface fastening system 40 attachment, creating a gap between the two regions. In a diaper 20, the outward and upward angle of the hinge line 11 helps keep the chassis 22 in place for a proper fit during use.

Figure 10:
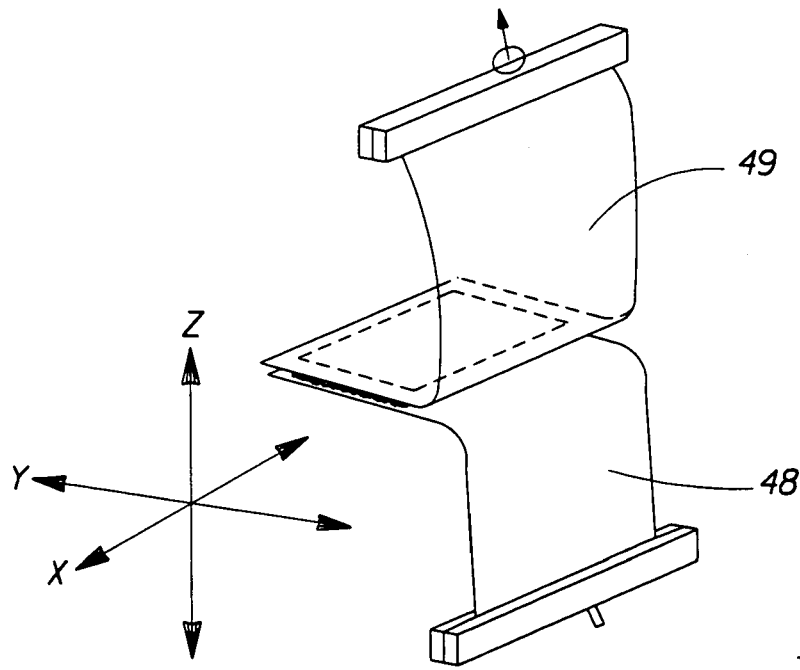
FIG. 10 is a three dimensional view of a perpendicular peel load test configuration.

A diaper 20 embodiment may have one or more hinge lines 11 that extend generally along the perimeter 341 of the low motion zone 340 between the leg openings 58 and the waist hoop 55. As shown in FIG. 10, shear load is load in the x and y plane of the fastened first and second fastening elements and peel load is in the yz through xz planes. The present invention allows the fastener to change it's orientation to the load and carry what would otherwise be a peel load as a shear load. The fastening system 40 reorients itself during peel loading by lifting the liftable portion 72 to transfer some of the applied load from a peel load to a shear load. Thus, the peel load capacity is increased by converting the peel load to a shear load with respect to the fastener by lifting the liftable portion 72. In a diaper 20, the designed surface fastening system 40 reorients the fastening interface when under load, for example loads created by movement of the wearers legs, allowing greater resistance to unintentional fastener disengagement.

The surface fastening system 40 may become disengaged in a peel mode and/or a shear mode. The peel mode exists when the first fastening element 49 is held stationary or pulled in a generally perpendicular or angled direction away from the second fastening element 48. The second fastening element 48 may be pulled off the first fastening element 49 sequentially by oppositely directed forces acting in a direction generally perpendicular or at an angle to the surfaces being separated as shown in FIG. 10. For example, in a hook and loop surface fastening system, each row or line of hooks may be disengaged a little at a time until all the hooks are disengaged from their respective loops. This results in the overall surface fastener being progressively disengaged from a first point to a second point such as from a first edge to a second edge. The peel performance of hook and loop systems is very sensitive to the cost/performance ratio. Generally, to obtain higher peel load resistance, a higher basis weight loop is used which ultimately translates to more loops, thicker fabric, stronger adhesives, and greater overall cost.

A shear mode of disengagement, in comparison, exists when the two components are being pulled apart by oppositely directed forces lying in the same plane as the surfaces being joined. The shear mode of disengagement is a sliding, linear action, in contrast to the peel mode disengagement that is a curvilinear type of motion or action. Generally, a surface fastening system 40 requires less peel force than shear force to disengage the surface fastening system 40. Thus, a surface fastening system 40 is more likely to fail in a peel mode than in a shear mode. A transfer of peel load to shear load may allow a lower basis weight loop or adhesive, which ultimately may translate to a lesser overall cost.

In one preferred embodiment of the present invention, a surface fastening system 40 provides for multi-directional resistance to peel mode disengagement. In a refastenable pull-on diaper, for example, the surface fastening system 40 may be subjected to forces in many directions as the diaper is pulled on over the wearer's feet, ankles, knees, buttocks, etc. The article is also subject to forces in many directions after application as the wearer moves their waist hips, buttocks and legs. It is preferable that the surface fastening system 40 not disengage when it is subjected to these forces. However, at the same time the surface fastening system 40 is preferably not difficult to disengage when the diaper is being intentionally removed from the wearer. Thus, it is preferable that the surface fastening system 40 have different levels of resistance to disengagement in different directions.

The surface fastening system 40 may generally comprises a peel load capacity when subject to a peel load and a shear load capacity when subject to a shear load, wherein the peel load capacity is increased by converting the peel load to the shear load by lifting the liftable portion 72. In one embodiment the surface fastening system 40 may have a peel load capacity that is greater than or equal to about 1000 grams, greater than about 1300 grams, greater than about 1600 grams, or greater than about 2000 grams.

FIG. 2 depicts a diaper 20 affixed on a wearer. The surface fastening system 40 preferably maintains the first waist region 36 and the second waist region 38 in a configuration so as to provide lateral tensions about the waist hoop 55 of the diaper 20 to hold the diaper 20 on the wearer. In a preferred embodiment, the surface fastening system 40 will fasten to the front of the wearer. Fastening to the front of the wearer may be accomplished by having the first fastening element 49 positioned on the article such that it is to the front of the wearer. FIG. 2 shows two axes, an x-axis generally oriented about the waist of the wearer and a y-axis generally oriented vertically on the wearer in a standing position. A z-axis is generally perpendicular to the x-axis and the y-axis and extends out of the plane of FIG. 2. In one embodiment, the x-axis defines the primary direction of load bearing. For a diaper, the x-axis primary direction of load bearing is lateral tension about the circumference (waist hoop 55) holding the diaper around the waist of the wearer.

Figure 3:
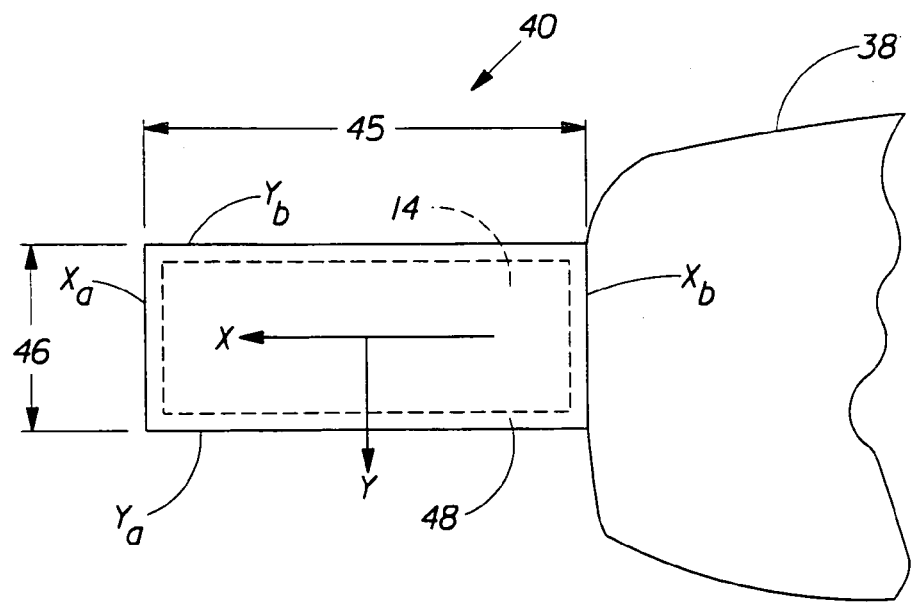
FIG. 3 is an expanded view of the second fastening element portion of the surface fastening system shown in FIG. 2.

In FIG. 3, the article may have a surface fastening system 40 such as a hook and loop, hermaphroditic, adhesive, cohesive and/or magnetic fastener. In one embodiment, the fastening system 40 is disengaged by the distal edge $X_a$. The distal edge $X_a$ is peeled away in the xz-plane such that the surface fastening system 40 is progressively disengaged by peeling from the distal edge $X_a$ to the proximal edge $X_b$ along the x-axis. Thus, the surface fastening system 40 preferably is not as difficult to peel in the xz-plane from the distal edge $X_a$ to the proximal edge $X_b$ (so that the diaper may be easily removed from the wearer), as it is to disengage under a peel load in the yz-plane (so that the diaper may remain affixed during normal use). Alternatively, at least a portion of the distal edge $X_a$ is preferably easier to remove in order to start the peeling action. Thus, it is preferable that at least a portion of the distal edge $X_a$ of the surface fastening system 40 is easy to disengage in a peel mode by a force located substantially in the xz-plane for at least a portion of the path from the distal edge $X_a$ to the proximal edge $X_b$. However, the surface fastening system 40 may become progressively more difficult to disengage as the peel mode disengagement progresses toward the proximal edge $X_b$.

The surface fastening system 40 includes longitudinally inboard edge $Y_a$ and longitudinally outboard edge $Y_b$ as shown in FIG. 3. Further, FIG. 2 depicts axes y' and y" that are offset from the y-axis by an angle α on either side of the y-axis. Preferably, the surface fastening system 40 is able to remain fastened when subjected to peel forces in all the planes between the y'z-plane and the y"z-plane, including the yz-plane when the peel forces act on the longitudinally inboard edge $Y_a$ and/or the longitudinally outboard edge $Y_b$. All planes extend in the positive and negative direction from the coordinate axis.

The surface fastening system 40 should usually remain fastened during normal use. Preferably, the surface fastening system 40 has a peel load capacity when subjected to peel forces during use in a direction other than in the xz-plane through y'z-plane that is greater than about 1000 grams, more preferably greater than about 1300 grams, even more preferably greater than about 1600 grams, and yet even more preferably greater than about 2000 grams. Generally, a surface fastening system 40 peel load capacity of between about 2000 grams and 6000 grams may be used. Preferably, the surface fastening system 40 peel force direction includes a direction in the y'z-plane through the y"z-plane. The angle α is preferably about 20 degrees, more preferably about 30 degrees, even more preferably about 40 degrees, yet even more preferably about 50 degrees and most preferably about 60 degrees.

Intentional fastening system disengagement during article removal, with or without lifting the liftable portion, occurs in the xz plane through y'z-plane. Preferably, at least a portion of the distal edge $X_a$ shown in FIG. 3, may become disengaged in a peel mode by a force oriented in the xz-plane through y'z-plane that is less than the force that will cause the surface fastening system 40 to become disengaged in a peel mode by a force in a direction other than in the xz-plane (e.g. the peel load required to intentionally release the fastening system in one peel direction is less that the peel load required to disengage the fastening system during use in a different peel direction). More preferably, at least a portion of the distal edge $X_a$ may become disengaged in a peel mode (e.g. intentional fastening system disengagement during article removal without lifting the liftable portion) by a peel force directed in the xz-plane which is less than or equal to about 1000 grams. Even more preferably at least a portion of the distal edge $X_a$ of the surface fastening system may become disengaged in a peel mode by a peel force directed in the xz-plane which is less than or equal to about 750 grams. Yet even more preferably at least a portion of the distal edge $X_a$ of the surface fastening system 40 may become disengaged in a peel mode by a peel force directed in the xz-plane less than or equal to about 500 grams.

The surface fastening system 40 of the present invention may be designed to achieve a certain resistance to peel mode disengagement. For example, changes in design, structure, attachment and/or material may affect the resistance of the surface fastening system 40 to peel mode disengagement. A change in design may include the dimension of the fastener at the edge that is resisting peel mode disengagement or the overall shape of the engaging area. A longer y-dimension 46, as shown in FIG. 3, for the fastening system 40 results in a greater resistance to peel mode disengagement along the longer y-dimension edge. For example, a surface fastening system 40 having a resistance to peel mode disengagement of about 800 grams along a 0.5 inch edge will generally have a resistance to peel mode disengagement of up to about 1600 grams at the edge if the length of the edge is increased to about one inch. Also, the overall shape of the engaging area of the surface fastening system 40 may be optimized to minimize the cost and/or difficulty in disengaging the surface fastening system 40 in one direction while maximizing the resistance to peel mode disengagement in another direction. On some surface fastening systems 40, the resistance to peel mode disengagement in various directions may also be selectively enhanced or reduced by enhancing or damaging portions of the fastening system 40 as disclosed later herein. Further, the structure may be modified in order to increase or decrease the resistance of the fastening system 40 to peel mode disengagement. One such embodiment of a modification would be by including a liftable portion 72 along a hinge line 11 such that it protects the y-dimension edge 46 of the fastening system 40 from disengaging in a peel mode.

The resistance to peel mode disengagement may also be affected by the selection of the fastening materials used in the surface fastening system 40. For example, some fastening materials have an inherently higher resistance to peel mode disengagement than other materials, commonly referred to as an aggressive fastener. Although use of an aggressive fastening material may increase the resistance to peel mode disengagement in the desired direction, the use of this material, in the absence of other design criteria, may result in an unacceptably high resistance to peel mode disengagement in another direction. In certain preferred embodiments, the surface fastening system 40 may have inherent directionality in peel resistance thus enabling peel to be maximized in one or more directions with minimal or no increase in peel in other directions. For example, hooks may be manufactured having an orientation as disclosed in U.S. Pat No. 6,054,091 issued to Miller, et al on Apr. 25, 2000 and U.S. Pat. No. 5,325,415 issued to Goulait, et al on Jul. 5, 1994, each of which is incorporated by reference. In such hooks or other fastening materials with inherent directionality, the orientation inherent in the raw material may not result in the desired orientation in the product. In such cases, the fastening material may be re-oriented during manufacture of the product in order to result in the desired directionality on the finished product.

When the wearer is active or when the diaper 20 is pulled onto the wearer, the surface fastening system 40 will also preferably remain fastened in the presence of peel forces in directions other than in the xz-plane. The first fastening element 49 and/or the second fastening element 48 may have a liftable portion 72 which is liftable in at least the xz-plane, allowing the surface fastening system 40, when fastened and under load, to move out of a more peel load bearing orientation with the load into a more shear load bearing orientation. Two or three-dimensional movement may be possible for the liftable portion 72 when surface fastening system 40 is fastened. Since fasteners generally may handle more shear load than peel load, the surface fastening system 40 load carrying capacity may be improved for loads that would otherwise be carried by the fastening system 40 in a peel orientation.

EXEMPLARY EMBODIMENTS

Some embodiments of the surface fastening systems 40 of the present invention are described in detail below. These examples are meant to describe several embodiments of the present invention and are non-limiting. One skilled in the art may be able to build different examples based upon the concepts taught in this detailed description in order to achieve the desired functional characteristics of the present invention.

The peel resistance in the yz and xz-planes of FIG. 2 may be different. One method of achieving different peel resistances is by changing the dimensions of the retaining element 14 in the xy-plane. FIG. 3 shows one example of a design in which the dimensions of the retaining element 14 is optimized for a higher resistance to peel mode disengagement in the yz-plane and a lower resistance to peel mode disengagement in the xz-plane. The fastening material includes two dimensions, an x-dimension 45 generally oriented along the x-axis, and a y-dimension 46 generally oriented along the y-axis as shown in FIG. 2. In this embodiment, the horizontal or x-dimension 45 is longer than the vertical or y-dimension 46. Thus, the resistance to peel mode disengagement may be greater in the yz-plane than in the xz-plane. In one particular embodiment, for example, the surface fastening system 40 may include a hook and loop fastener in which at least the engaged area in common between the hook fastening element and the loop fastening element have the shape as shown in FIG. 3 when configured as intended for use of the article. The hook fastening element, for example, may have an x-dimension 45 of about 1.0 inch and a y-dimension 46 of about 0.5 inch. The loop fastening element may have the same or larger dimensions as the hook material. In this embodiment, the resistance to peel mode disengagement in the yz-plane may be about twice that of the resistance to peel mode disengagement in the xz-plane for hook and loop systems with minimal inherent directionality. Alternatively in this example, the resistance to peel mode disengagement in the yz-plane may be greater than twice the resistance to peel mode disengagement in the xz-plane if the hook and loop system has high inherent directionality with peel maximized for the yz-plane direction. By altering the x-dimension 45 relative to the y-dimension 46, preferred ranges of yz-plane peel resistance and xz-plane peel resistance can be achieved.

Figure 4A:
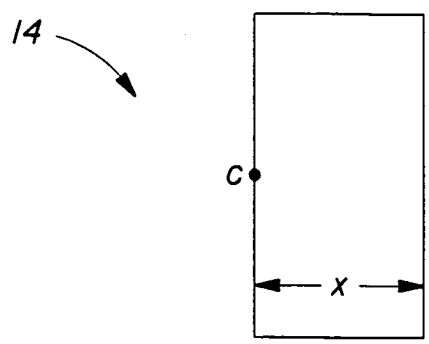
FIGS. 4A through 4D are plan views of alternative embodiments of a surface fastening system retaining element.
Figure 4B:
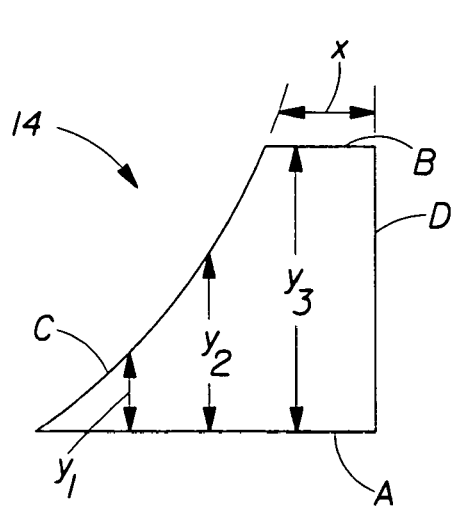
Figure 4C:
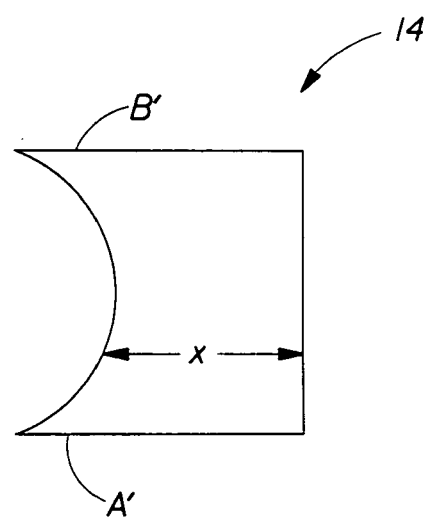
Figure 4D:
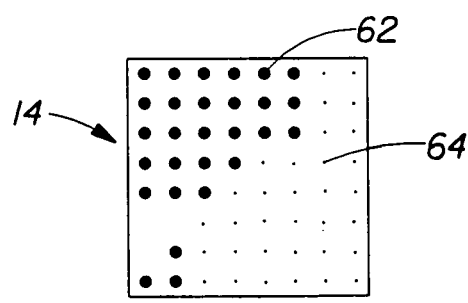
Figure 5A:
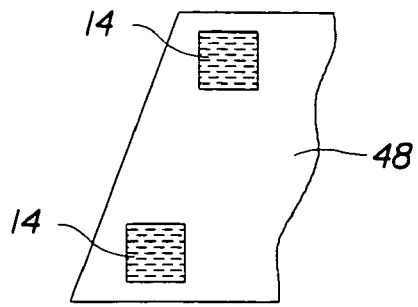
FIGS. 5A-D depict possible retaining element configurations.
Figure 5B:
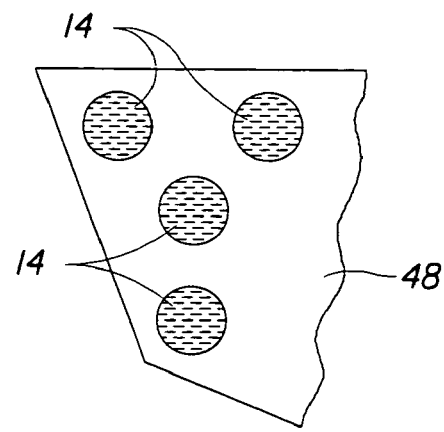
Figure 5C:
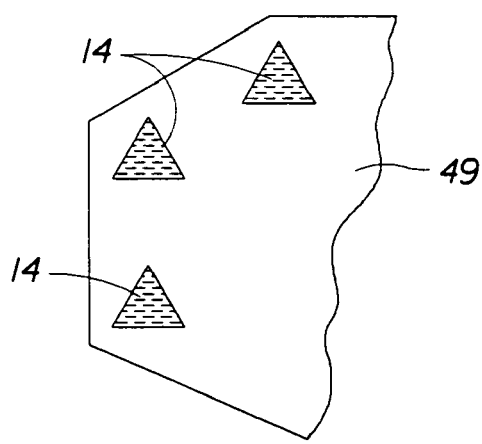
Figure 5D:
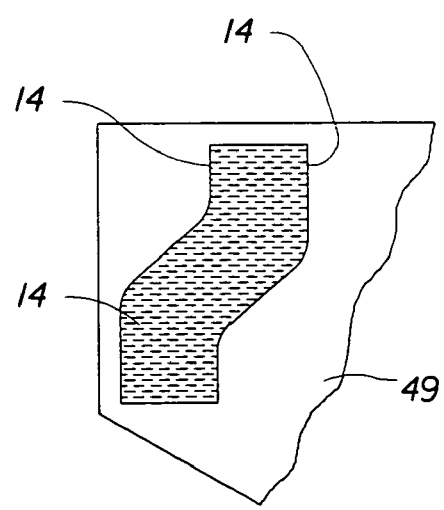

In another embodiment, the shape of the retaining element 14 may be optimized for a higher resistance to peel mode disengagement in, for example, the yz-plane and a lower resistance to peel mode disengagement in, for example, the xz-plane. FIGS. 4A through 4C, for example, show possible shapes of retaining elements 14 that may be used in a surface fastening system 40. Generally, the surface fastening system 40 and/or fastening elements will comprise at least one retaining element 14. FIG. 4A shows a typical rectangular-shaped retaining element 14. FIG. 4B shows one embodiment of a retaining element 14 of the present invention in which the shape of the retaining element 14 has been designed in order to decrease the resistance to peel mode disengagement in the yz-plane as peel progresses from edge A to edge B by decreasing an effective dimension X along at least a portion of the path from edge A to edge B. Thus, the resistance to yz-plane peel is initially higher at edge A and may decrease at some point between edge A and edge B. The initial peel resistance at the laterally inboard edge C, however, has been decreased by shaping the laterally inboard edge C so that the effective dimension X in the y-direction increases for at least a portion of the path from edge C to laterally outboard edge D. For example, as shown in FIG. 4B, y-dimension Y1 is smaller than Y2 and Y3. Thus, resistance to peel in the xz-plane increases from Y1 to Y3. In one particular embodiment, the surface fastening system 40 retaining element may include a hook and loop fastener shaped as shown in FIG. 4B. In FIG. 4B, the effective length of dimension Y increases along at least a portion of the path from edge C to edge D, and the effective dimension X decreases along at least a portion of the path from edge A to edge B. In certain embodiments such as shown in FIG. 4C, the effective dimension X may initially decrease or increase along a portion of the path from edge A' to edge B' then increase or decrease along another portion of the path from edge A' to edge B'.

In alternative embodiments, the peel resistance of a surface fastening system 40 may be selectively altered by varying the effective shape of the retaining element 14 of the surface fastening system 40 in addition, or as an alternative to, altering the actual shape of the retaining element 14 of surface fastening system 40 as discussed above. For example, FIG. 4C shows another particular embodiment of a surface fastening system 40 of the present invention in which a generally rectangular patch of retaining element 14 fastening material is rendered effectively trapezoidal shaped by selectively damaging a portion of the retaining element 14. For example, portions of the retaining element 14 may be damaged such as by mechanical bonding, ultrasonic bonding, selective heating, or any other process capable of disabling a portion of a fastening element. In this embodiment, a first portion 62 of the retaining element 14 may be selectively damaged in order to lower the peel resistance of the surface fastening system 40 in that area, and a second portion 64 may be used to provide a higher peel resistance in an area where the higher peel resistance is desired.

Figure 6A:
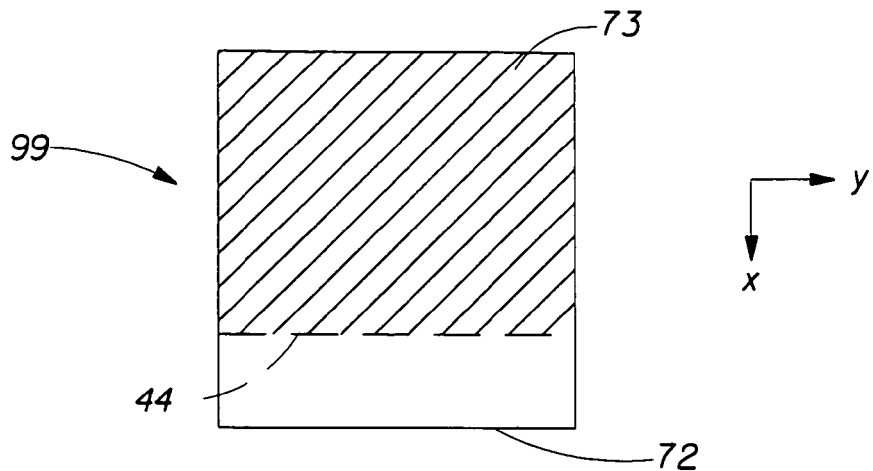
FIGS. 6A and 6B are a plan view of an alternative embodiment of a first fastening element.
Figure 6B:
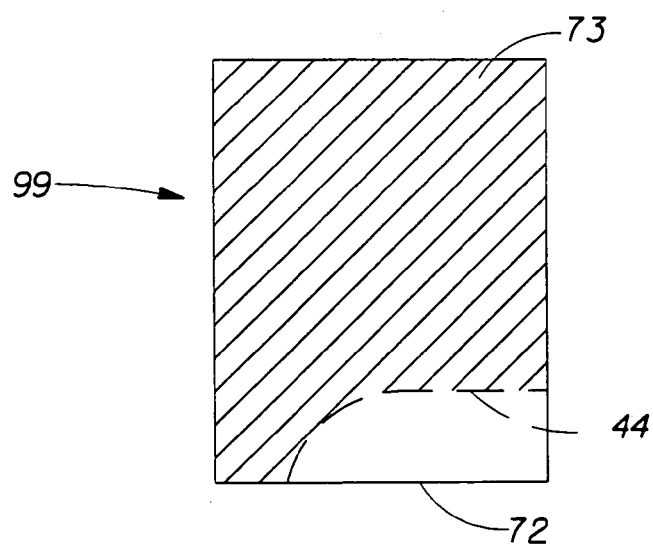
Figure 6C:
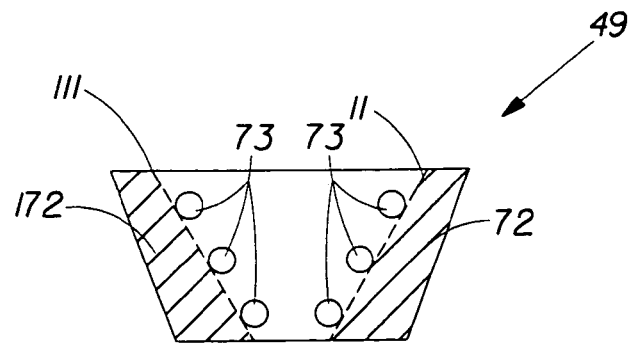
FIG. 6C depicts a plan view of two hinge lines defined by a collection of attached portions.

FIGS. 6A and 6B show embodiments in which the peel resistance of the surface fastening system 40 may be selectively enhanced. In FIGS. 6A and 6B, for example, liftable portion 72 of first fastening element 99 may be unjoined from the underlying structure of the article 20. In these figures, the attached portion 73 of the first fastening element 99, which may be joined to the underlying structure of the article 20, is shown crosshatched. The liftable portion 72 extends from the attached portion 73 along the hinge line 44. As used herein, extending from includes the liftable portion 72 being adjacent to or connected to attached portion 73. In this embodiment, all or a portion of the liftable portion 72 of the first fastening element 99 is free to pull away from the underlying structure of the article. This may increase the peel resistance of the surface fastening system 40. Without being bound by theory, it is believed that as the liftable portion 72 pulls away from the underlying structure of the article, the disengagement mode shifts gradually away from a peel mode to a shear mode of disengagement. In many surface fasteners such as a hook and loop fastener, it is generally more difficult to disengage the fastener in shear mode than in peel mode. Thus, the resistance to disengagement of the fastening system 40 to a force generated during the use of the article in the yz-plane through xz-plane (peel force) may be increased.

The above described approaches may be used alone or in combination to achieve the desired peel resistance in the yz- and xz-planes. Thus, by changes in design, structure, attachment and/or material, a system may be created to meet the functional requirements defined herein for resistance of the surface fastening system 40 to peel mode disengagement.

The fastening system 40 may be pre-fastened before application to the wearer. This allows the article to be used as a pull-on type diaper, such as a training pant. In other preferred embodiments, the product may be delivered to the consumer at least partially pre-fastened. For example, second fastening elements 48 of the surface fastening system 40 may be joined with a first fastening element(s) 49 during the article's manufacture in order to pre-fasten the surface fastening system 40. This may be accomplished by any means known in the art including for example adhesive and/or hook and loop. Pre-fastening of the article during its manufacture allows the consumer to slip the product over the wearer's feet and pull it in place about the torso as one does a traditional pull on article. Yet, the fasteners enable the user to disengage the fasteners if they so choose and fasten the article about the wearer without needing to remove lower body clothing, such as pants, stockings, or shoes.

Figure 7:
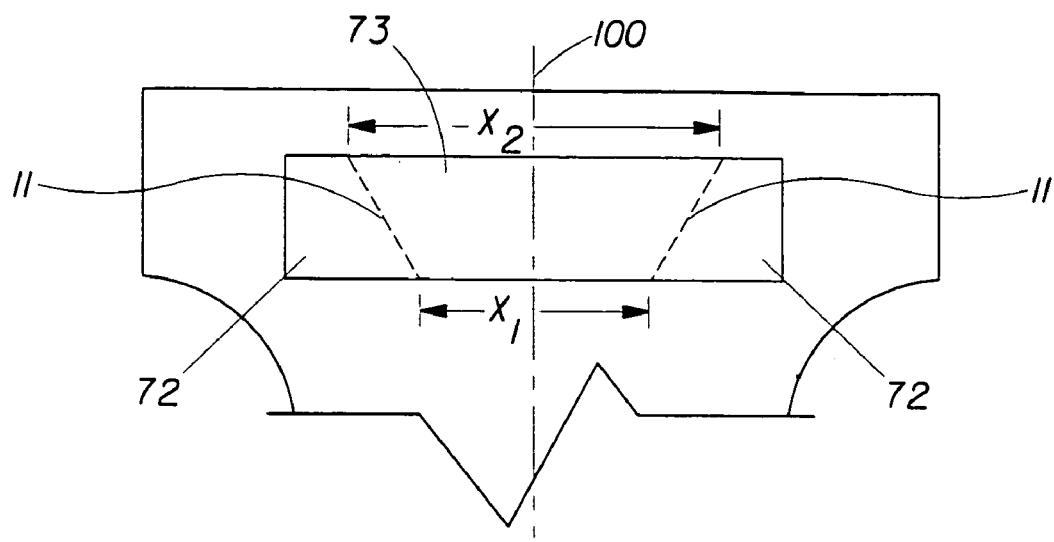
FIG. 7 is a plan view of a first fastening element with two hinge lines separated at distances X1 and X2.

In another embodiment, shown in FIG. 7, the first fastening element 49 has two divergent hinge lines 11, one on each side of the longitudinal centerline 100 of the diaper 20. The distance between the hinge lines 11 at a point closest to the lateral centerline 110 is defined as a distance X1. The distance between the hinge lines 11 at the point furthest from the lateral centerline 110 is defined as a distance X2. In one embodiment of the present invention, X1 is always less than X2. In another embodiment, X1 is about 60 mm or less. In another embodiment X2 is about 130 mm or larger.

Regardless of orientation of the hinge line 11, the retaining element 14 may be oriented parallel to the lateral centerline 10 of the product or at any angle relative to the lateral centerline 110 as shown in FIG. 9. A preferred embodiment includes a hinge line 11 and retaining element 14 of the first fastening elements 49 both oriented such that they intersect (at an angle other than parallel to) the lateral centerline 110. The hinge line 11 and retaining element 14 of the second fastening element 48 may also be oriented such that they intersect (at an angle other than parallel to) the lateral centerline 110.

Figure 12:
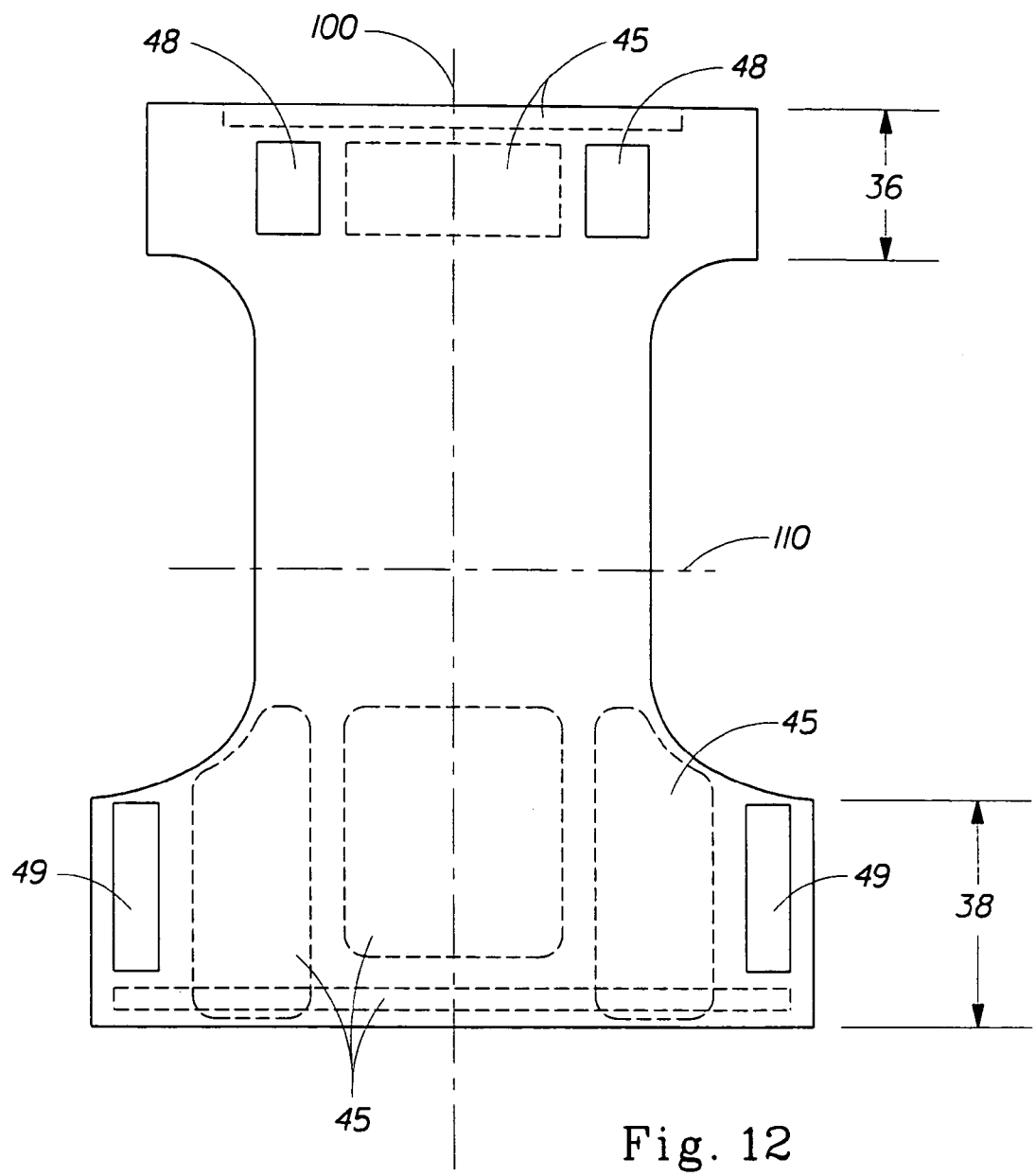
FIG. 12 is a plan view of one embodiment of the present invention in a flat configuration with possible elastomeric and/or fastener locations identified.

In a diaper 20 embodiment, the side panel 30, backsheet 26, and/or a surface fastening system 40 component such as the first fastening element 49, first fastening element liftable portion 72, and/or second fastening element 48 may include extensible and/or elastomeric materials. The extensible and/or elastomeric materials may provide a better fit or improved wearer comfort. The extensible and/or elastomeric materials may also allow the product to be used as a pull-on article. Pull-on usage would include fastening the first fastening element 49 to the second fastening element(s) 48 prior to putting the article on the wearer. Extensible material allows increased path length of stretchable materials around the leg to provide further freedom for leg movements in various article embodiments. The location of the extensible and/or elastomeric materials may vary. Possible extensible and/or elastomeric material locations 31 are shown in FIG. 12. These locations include the first waist region 36, and the second waist region 38. A preferred embodiment may have an angled elastomeric material locations 31 on the article side panel(s) 30, providing more stretch at the wearer's hips and less around the wearer's leg openings when the article worn by the wearer.

Figure 15A:
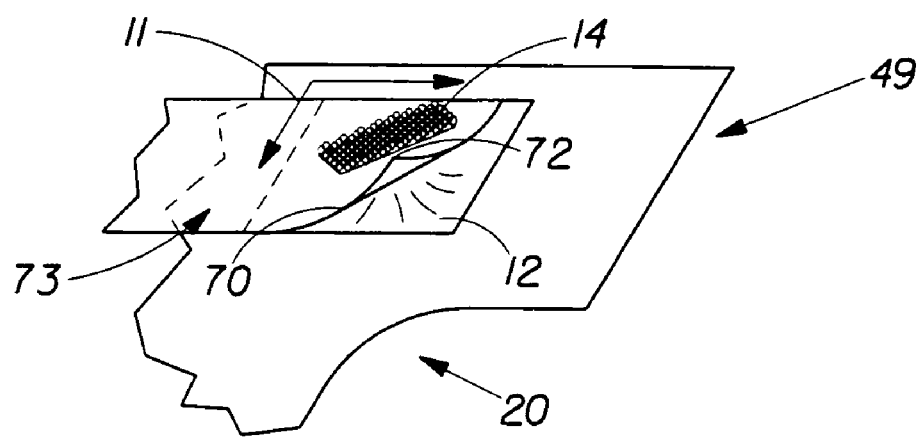
FIG. 15A is a perspective view of one embodiment of the first fastening zone with a masking element.
Figure 15B:
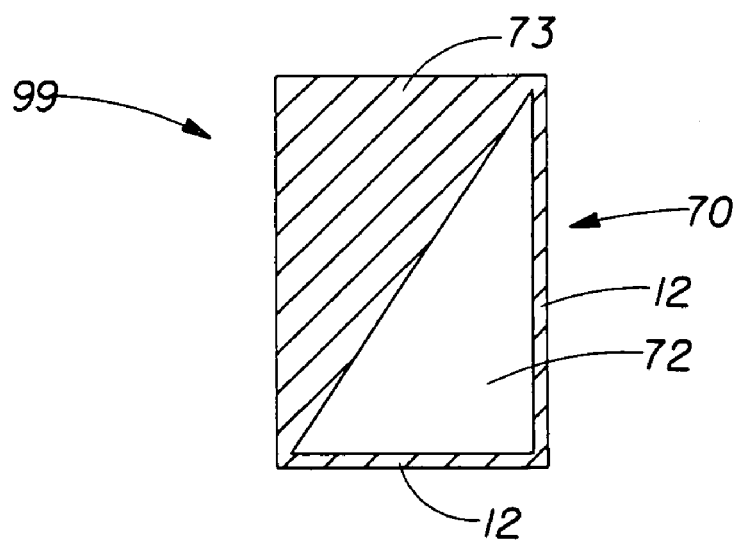
FIG. 15B is a plan view of an alternative embodiment of a first fastening element with a masking element.
Figure 16A:
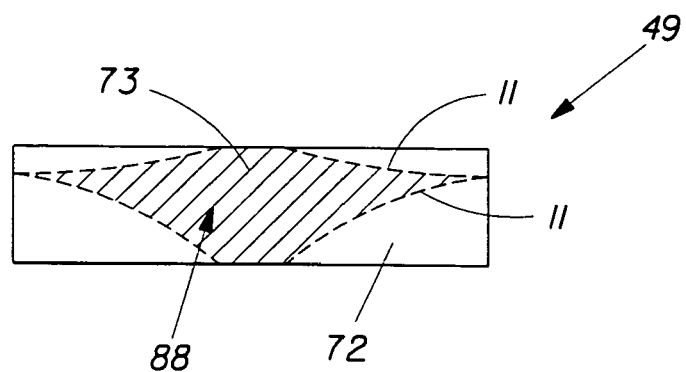
FIGS. 16A-16D depict a plan view of potential stiffening element locations.
Figure 16B:
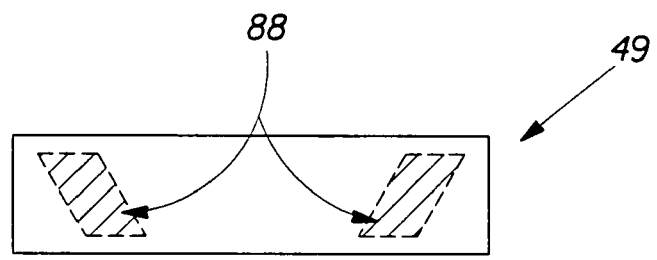
Figure 16C:
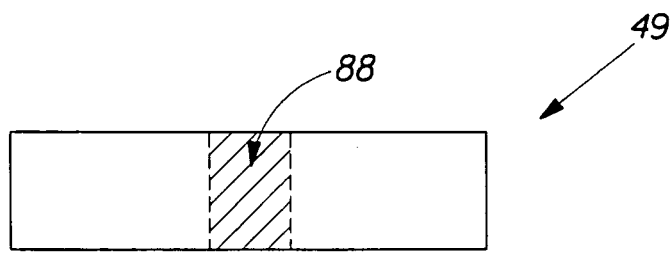
Figure 16D:
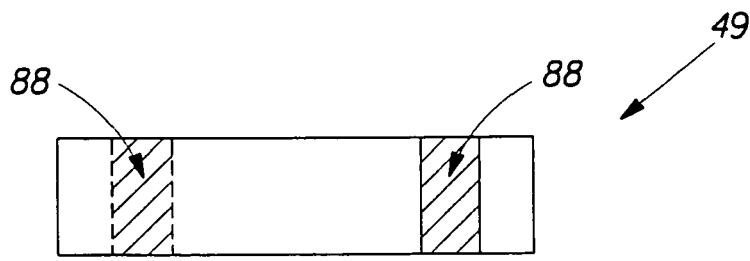

In another embodiment shown in FIG. 15A, a masking element 12 may be used to make less visible to an observer the lifting of liftable portion 72. The masking element 12 may at least partially surround liftable portion 72. A planar view of this embodiment is shown in FIG. 15B. The masking element 12 may be attached to the backsheet 26 and the liftable portion 72. In other embodiments the masking element 12 may be attached to the backsheet 26, the retaining element 14, first fastening element 49, second fastening element 48, or combinations and components thereof. It may be preferred to have the masking elements 12 be extensible or elastomeric. However, the masking element 12 may be non-extensible and non-elastomeric and gathered to provide sufficient path length for lifting the liftable portion 72 from the underlying article 20 as shown in FIG. 15A.

Figure 13:
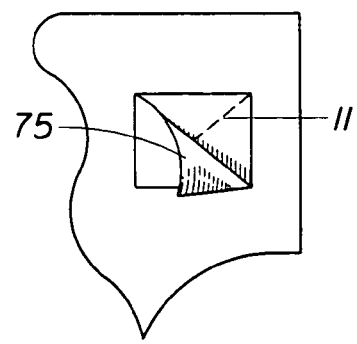
FIG. 13 is a plan view of one embodiment of the first fastening element with a flap.
Figure 14A:
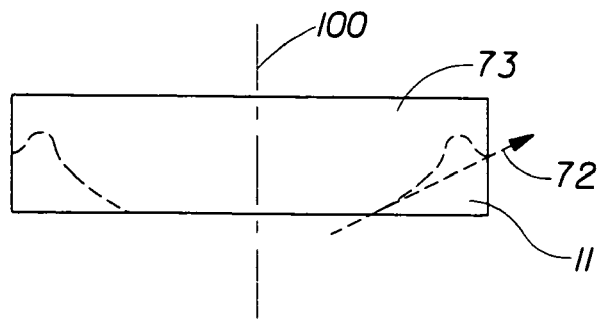
FIGS. 14A-14D are plan views of various first fastening element hinge line configurations.
Figure 14B:
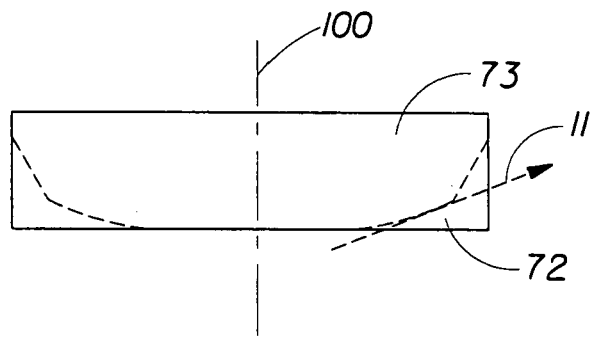
Figure 14C:
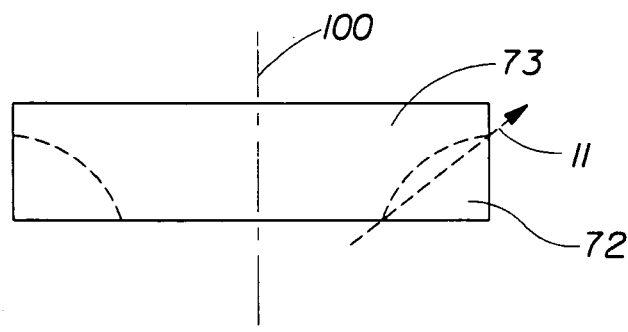
Figure 14D:
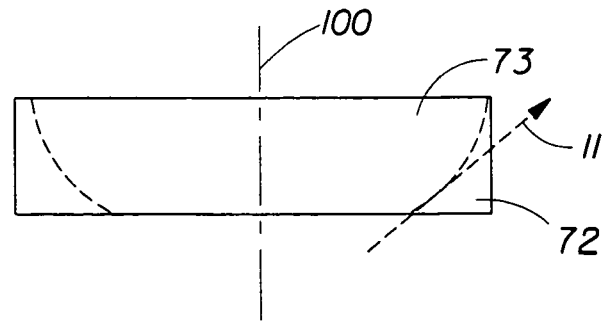

The first fastening member may include a flap 75 that is attached to the first fastening element 49 as shown in FIG. 13, or any other part of the article 20. The flap 75 may contain a retaining element 14 that engages with the second fastening element 48 on the surface opposite the first fastening element when the first and second fastening elements are engaged. The second fastening element would have retaining elements 14 of two sides, one side would engage the first fastening element 49 and the other would engage the flap 75. The additional flap 75 retaining elements 14 and second fastening element 48 retaining elements 14 provide additional fastening strength to the fastener system 40. Further details of a flap configuration are available in previously referenced U.S. patent application Ser. No. 09/633,422. Previously incorporated by reference.

Supplemental stiffening elements 88 function to reduce the flexibility of the diaper 20 waist and improve the articles visual appearance. The surface fastening system 40 may include supplemental stiffening elements 88 to provide the best overall fit and reduce roping, especially at the waist 55 of a diaper 20 as shown in FIG. 2. FIGS. 16A-16D show embodiments of the first fastening element 49 which contain one or more stiffening element(s) 88. The stiffening elements 88 may further reduce article roping or other undesirable deformation during article use. Generally, the stiffening element 88 may comprise a component of the article, e.g. diaper 20. The stiffening element 88 may be part of the surface fastening system 40 including the first fastening element 49, second fastening element 48, any attached portion 73, any unattached portion 72, or in combination thereof. The stiffening element 88 may be made from any material known it the art and may be made by any process known in the art. Preferable materials include plastic and paper products. Other processes could include making the first fastener 49 thicker in some locations or adding a stiffening catalyst to those portions of the fastening system in which a stiffening zone is desired.

Figure 17:
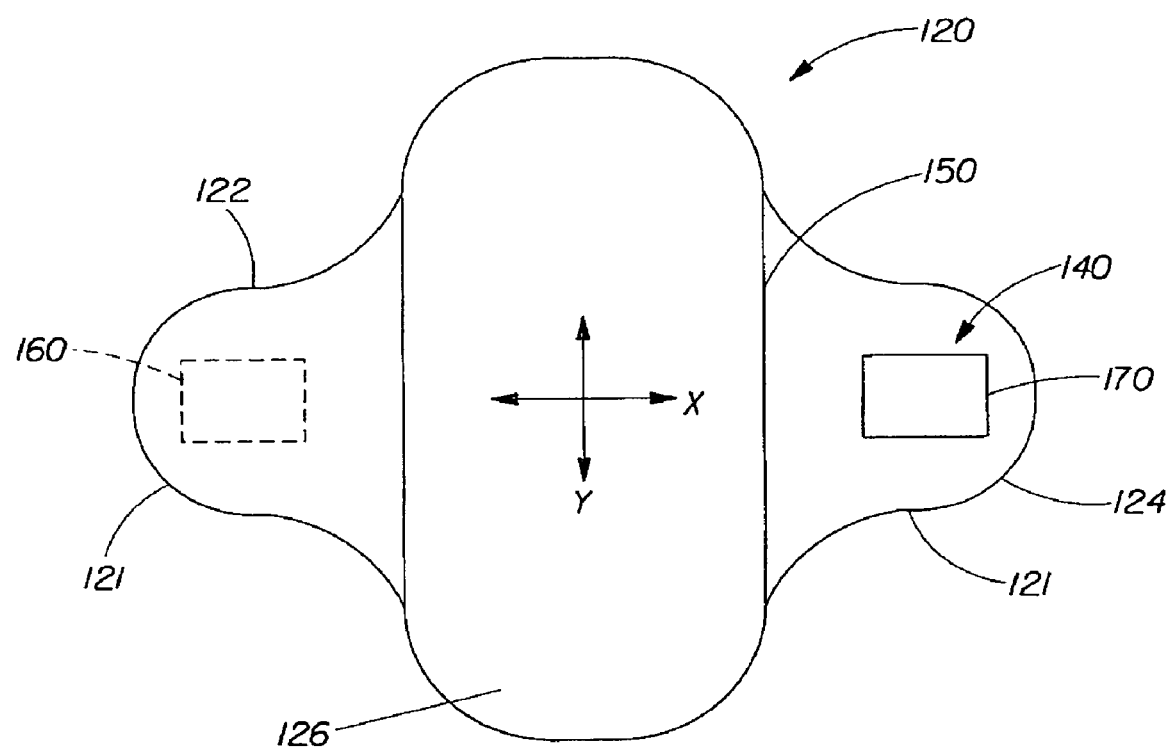
FIG. 17 is a plan view of a sanitary napkin alternative embodiment.

FIG. 17 shows an example of an alternative embodiment of the present invention such as a sanitary napkin or light incontinent pad that includes the surface fastening system 140 of the present invention to hold the sanitary napkin or light incontinent pad in a configuration wrapped around a wearer's panties or underwear. For example, the fastening system 140 may be used to fasten first wing 122 and second wing 124 of a sanitary napkin 120 about a wearer's panties. Fastening the wings of a sanitary napkin 120 about the wearer's undergarment may help ensure that the sanitary napkin 120 will stay in place while in use and provides a means for reducing the likelihood that the undergarment will be soiled if the core of the sanitary napkin 120 should leak. The fastening system 140 of the sanitary napkin 120, for example, may include a first fastening element 160 and a second fastening element 170. As shown in FIG. 17, for example, the first fastening element 160 may be located on the first wing 122 and the second fastening element 170 may be located on the second wing 124. The wings 121 extend outwardly from the longitudinal edges 150 of the sanitary napkin 120. Alternatively, the first fastening element 160 or the second fastening element 170 may be disposed on a portion of the backsheet 126 of the sanitary napkin 120 in a configuration similar to any of the embodiments described above with respect to a diaper 20. As described above with respect to other embodiments of the present invention, the fastening elements 160 and 170 may comprise any known surface fastening means, such as hooks, loops, adhesive, cohesive, magnets, and the like, or any combination of any of these fasteners. The first fastening element 160 and/or the second fastening element 170 may also include any of the surface fastening system 40 embodiments described above. Although the surface fastening system 140 is shown in FIG. 17 as the primary fastening device, the surface fastening system 140 of the present invention may be used in conjunction with other means for securing the napkin 120 to the undergarment or around the undergarment. Other suitable means include adhesives, cohesives, hooks, loops, friction, static, magnets, and/or any other means known in the art. The surface fastening system 140 may also be used to fasten the sanitary napkin 120 to other devices such as belts or other sanitary guards, or may be used as a means for wrapping the sanitary napkin 120 in a disposal configuration. Examples of sanitary napkins 120 with which the fastening system 140 of the present invention may be used are described in detail in U.S. Pat. No. 5,267,992 entitled "Shaped Sanitary Napkin With Flaps" issued to Van Tilburg on Dec. 7, 1993, and U.S. Pat. No. 5,389,094 entitled "Absorbent Article Having Flaps and Zones of Differential Extensibility" issued to Lavash et al. on Feb. 14, 1995, each of which is incorporated by reference herein.

Figure 18:
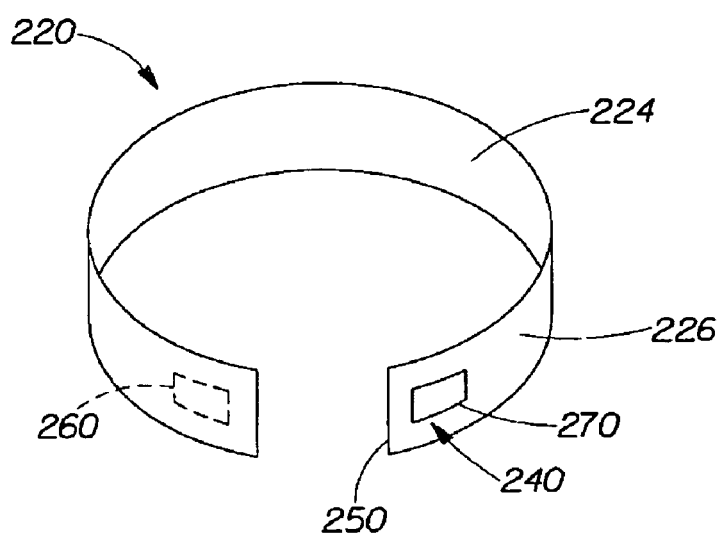
FIG. 18 is a perspective view of a body wrap alternative embodiment.

In yet another embodiment, a body wrap 220 may include a fastening system 240 of the present invention to hold the body wrap 220 in a fastened configuration around a portion of a wearer's body such as around the wearer's waist, torso, leg, ankle, foot, arm, wrist, hand, neck, head, etc. FIG. 18, for example, shows one possible embodiment of a body wrap 220 of the present invention having a fastening system 240 including a first fastening element 260 and a second fastening element 270. The first fastening element 260 and the second fastening element 270 may extend outwardly from an end edge 250 of the body wrap 220. Alternatively, the first fastening element 260 and/or the second fastening element 270 may be disposed on a portion of an inner surface 224 or an outer surface 226 of the body wrap 220. Further, the first fastening element 260 and/or second fastening element 270 may include any of the embodiments described above. One or more of the first fastening element 260 or the second fastening element 270 may include one or more surface fastening elements such as retaining element 14 disposed on one or more surface of the body wrap 220, and the fastening elements 260 and 270 may comprise any known surface fastening means, such as those described above. Examples of body wraps 220 with which the surface fastening system 140 of the present invention may be used are described in detail in U.S. Pat. No. 5,741,318 entitled "Elastic Back Wrap Having Diamond-Shaped Thermal Pattern and Anti-slip Means" issued to Oullette et al. on Apr. 21, 1998, and U.S. Pat. No. 5,860,945 entitled "Disposable Elastic Thermal Knee Wrap" issued to Cramer et al. on Jan. 19, 1999, each of which is incorporated by reference herein.

While particular embodiments and/or individual features of the present invention have been illustrated and described, it would be clear to those skilled in the art that various other changes and modifications can be made without departing from the spirit and scope of the invention. Further, it should be clear that all combinations of such embodiments and features are possible and can result in preferred executions of a invention. Therefore, the appended claims are intended to cover all such changes and modifications that are within the scope of this invention.

What is claimed is:

1. An article having a surface fastening system, the surface fastening system including:
   a) a first fastening element comprising:
      a retaining element;
      an attached portion joined to the article, said attached portion being fully or intermittently attached to the article;
      a liftable portion extending from the attached portion, wherein at least about 5% of the retaining element is located on the liftable portion, said liftable portion being adapted to be lifted away from the article;
      a hinge line positioned between the attached portion and the liftable portion; and
   b) a second fastening element comprising:
      a retaining element, wherein at least a portion of the retaining element of said second fastening element is configured to be releasably engageable with at least a portion of the liftable portion of said first fastening element;
      an attached portion joined to the article;
      a liftable portion extending from the attached portion of said second fastening element wherein at least about 5% of the retaining element of the second fastening element is located upon the second fastening element liftable portion; a hinge line positioned between the attached portion and the liftable portion of said second fastening element, said article comprising a primary direction of load bearing, the primary direction of load bearing intersecting the hinge line of at least one of said first and second fastening elements at an angle of less than 90 degrees.

2. The article of claim 1, wherein the liftable portion of the first fastening element is configured to be releasably engageable with the liftable portion of the second fastening element.

3. An article having a surface fastening system, the surface fastening system including:
   a) a first fastening element comprising:
      a retaining element;
      an attached portion joined to the article, said attached portion being fully or intermittently attached to the article;
      a liftable portion extending from the attached portion, wherein at least about 5% of the retaining element is located on the liftable portion, said liftable portion being adapted to be lifted away from the article;
      a hinge line positioned between the attached portion and the liftable portion; and
   b) a second fastening element comprising:
      a retaining element, wherein at least a portion of the retaining element of said second fastening element is configured to be releasably engageable with at least a portion of the liftable portion of said first fastening element;
      an attached portion joined to the article;
      a liftable portion extending from the attached portion of said second fastening element wherein at least about 5% of the retaining element of the second fastening element is located upon the second fastening element liftable portion; a hinge line positioned between the attached portion and the liftable portion of said second fastening element, said article comprising wherein the peel load capacity during use is greater than or equal to about 1000 grams.

4. An article having a surface fastening system, the surface fastening system including:
   a) a first fastening element comprising:
      a retaining element;
      an attached portion joined to the article, said attached portion being fully or intermittently attached to the article;
      a liftable portion extending from the attached portion, wherein at least about 5% of the retaining element is located on the liftable portion, said liftable portion being adapted to be lifted away from the article;
      a hinge line positioned between the attached portion and the liftable portion; and
   b) a second fastening element comprising:
      a retaining element, wherein at least a portion of the retaining element of said second fastening element is configured to be releasably engageable with at least a portion of the liftable portion of said first fastening element;
      an attached portion joined to the article;
      a liftable portion extending from the attached portion of said second fastening element wherein at least about 5% of the retaining element of the second fastening element is located upon the second fastening element liftable portion; a hinge line positioned between the attached portion and the liftable portion of said second fastening element, said article comprising wherein the surface fastening system may be disengaged in a peel mode through intentional surface fastening system disengagement with a peel load of less than about 1000 grams.

5. The article of claim 4, wherein the first fastening element is positioned on the front of the wearer.

6. The article of claim 4, wherein the article includes a disposable diaper, sanitary napkin, pant-like garment, body wrap, or medical bandage.

7. The article of claim 4, wherein the article includes a liquid pervious topsheet, a liquid impervious backsheet and an absorbent core interposed between the topsheet and the backsheet.

8. The article of claim 4, further comprising opposite side panels and at least two second fastening elements, the second fastening elements being disposed on the opposite side panels so as to be generally attachable in a face to face relationship with at least a portion of the liftable portion of the first fastening element when the surface fastening system is in a fastened configuration.

9. The article of claim 4, wherein the first fastening element includes a flap with a retaining element.

10. The article of claim 4, wherein the first fastening element includes a masking element.

11. The article of claim 4, wherein the first fastening element includes a stiffening element.

12. The article of claim 4, wherein the liftable portion of the first and/or second fastening element includes an elastomeric portion.

13. The article of claim 4, wherein the first fastening element and the second fastening element are pre-fastened.

14. An article having a surface fastening system, the surface fastening system including:
   a) a first fastening element comprising:
      a retaining element;
      an attached portion joined to the article, said attached portion being fully or intermittently attached to the article;
      a liftable portion extending from the attached portion, wherein at least about 5% of the retaining element is located on the liftable portion, said liftable portion being adapted to be lifted away from the article;
      a hinge line positioned between the attached portion and the liftable portion; and
   b) a second fastening element comprising:
      a retaining element, wherein at least a portion of the retaining element of said second fastening element is configured to be releasably engageable with at least a portion of the liftable portion of said first fastening element;
      an attached portion joined to the article;
      a liftable portion extending from the attached portion of said second fastening element wherein at least about 5% of the retaining element of the second fastening element is located upon the second fastening element liftable portion; a hinge line positioned between the attached portion and the liftable portion of said second fastening element, said article comprising a longitudinal centerline wherein the longitudinal centerline is intersected by the hinge line of at least one of said first and second fastening elements.

15. The absorbent article of claim 14, further comprising a lateral centerline wherein the hinge line of at least one of said first and second fastening elements intersects the longitudinal centerline and the lateral centerline.

* * * * *

UNITED STATES PATENT AND TRADEMARK OFFICE
CERTIFICATE OF CORRECTION

PATENT NO.       : 7,384,415 B2
APPLICATION NO.  : 10/774259
DATED            : June 10, 2008
INVENTOR(S)      : Mark J. Kline et al.

It is certified that error appears in the above-identified patent and that said Letters Patent is hereby corrected as shown below:

Column 3
Line 59, delete "previous" and insert -- pervious --.

Column 18
Line 3, delete "10" and insert -- 110 --.

Signed and Sealed this

Sixteenth Day of December, 2008

JON W. DUDAS
*Director of the United States Patent and Trademark Office*